United States Patent [19]

Takenouchi

[11] Patent Number: 4,618,556

[45] Date of Patent: Oct. 21, 1986

[54] DEVELOPER AND DEVELOPING METHOD

[75] Inventor: Masanori Takenouchi, Urawa, Japan

[73] Assignee: Canon Kabushiki Kaisha, Tokyo, Japan

[21] Appl. No.: 751,994

[22] Filed: Jul. 3, 1985

Related U.S. Application Data

[63] Continuation-in-part of Ser. No. 522,501, Aug. 12, 1983, abandoned.

[30] Foreign Application Priority Data

| Aug. 23, 1982 | [JP] | Japan | 57-145823 |
| Sep. 3, 1982 | [JP] | Japan | 57-154127 |
| Sep. 8, 1982 | [JP] | Japan | 57-157156 |
| Sep. 8, 1982 | [JP] | Japan | 57-157157 |
| Dec. 29, 1982 | [JP] | Japan | 57-231526 |
| Dec. 29, 1982 | [JP] | Japan | 57-231527 |
| Mar. 8, 1983 | [JP] | Japan | 58-37705 |
| Mar. 8, 1983 | [JP] | Japan | 58-37706 |
| Mar. 9, 1983 | [JP] | Japan | 58-39807 |
| Apr. 7, 1983 | [JP] | Japan | 58-61884 |

[51] Int. Cl.$^4$ ............................................. G03G 9/08
[52] U.S. Cl. .................................. 430/110; 428/404
[58] Field of Search ...................... 430/110; 428/404

[56] References Cited

U.S. PATENT DOCUMENTS

| 3,617,333 | 11/1971 | Brown | 428/404 X |
| 3,720,617 | 3/1973 | Chatterji et al. | 430/110 |
| 3,983,045 | 9/1976 | Jugle et al. | 430/110 |
| 4,039,331 | 8/1977 | Lee | 430/110 X |
| 4,072,796 | 2/1978 | Reinhardt et al. | 428/405 |
| 4,499,168 | 2/1985 | Mitsuhashi | 430/99 |

FOREIGN PATENT DOCUMENTS

| 2630564 | 1/1977 | Fed. Rep. of Germany . |
| 53-3237 | 1/1978 | Japan . |
| 5135835 | 10/1980 | Japan . |
| 1347318 | 2/1974 | United Kingdom . |
| 1402010 | 8/1975 | United Kingdom . |

Primary Examiner—John D. Welsh
Attorney, Agent, or Firm—Fitzpatrick, Cella, Harper & Scinto

[57] ABSTRACT

A developer for electrostatography containing a positive charge controlling agent comprising fumed silica particles treated with a silane coupling agent or titanate coupling agent and controlled to an appropriate degree of hydrophobicity has a stable and sharp distribution in amount of positive triboelectric charges under a variety of conditions including higher temperature-higher humidity or lower temperature-lower humidity conditions. This developer is useful particularly in an electrophotographic process employing a developer carrying member for charging of the developer.

18 Claims, 18 Drawing Figures

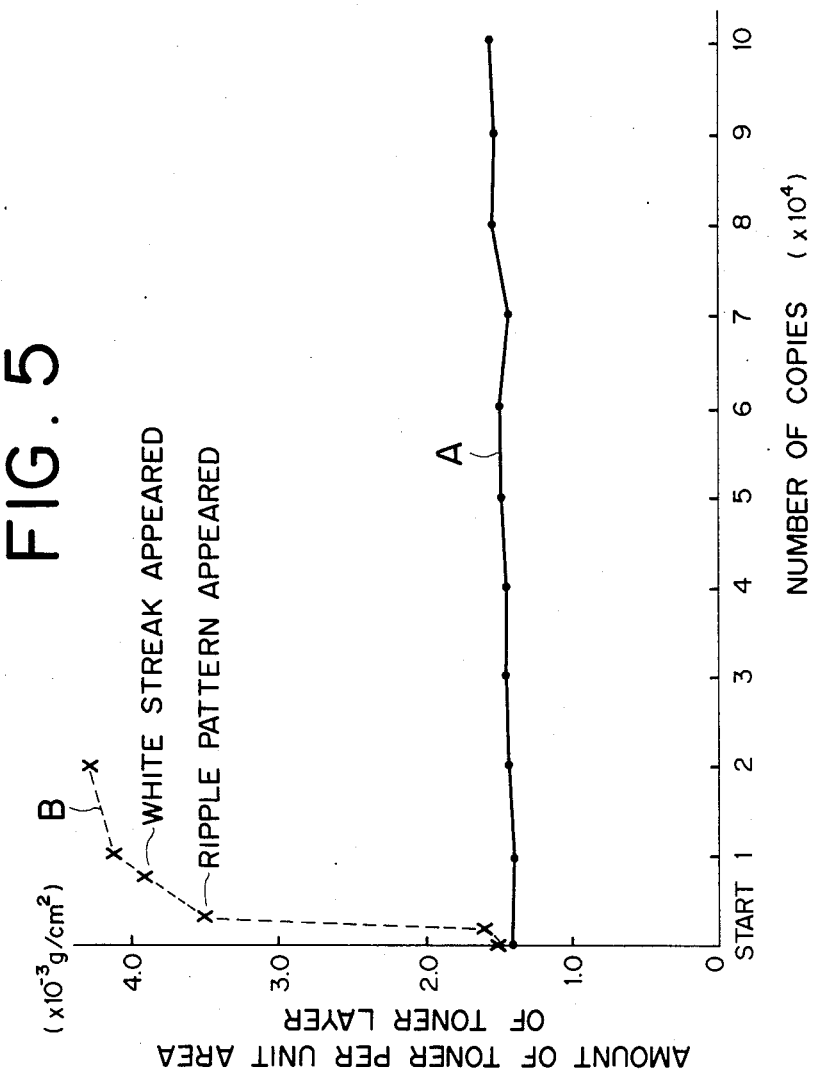

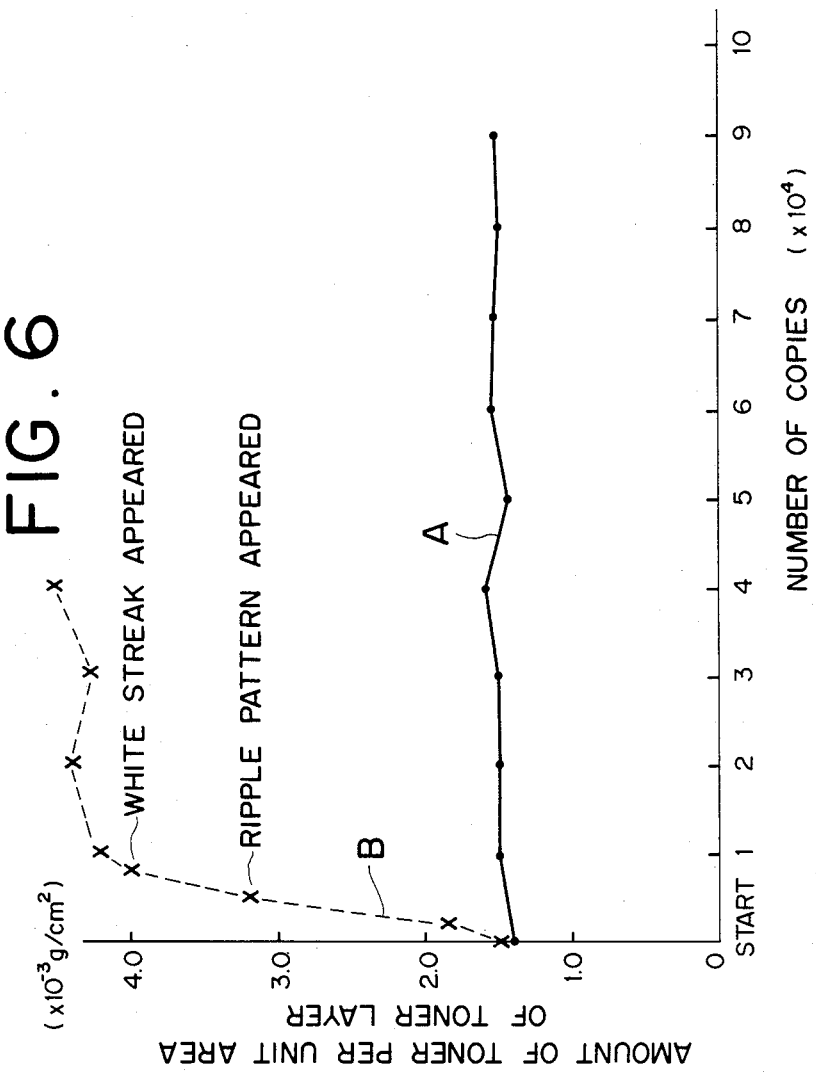

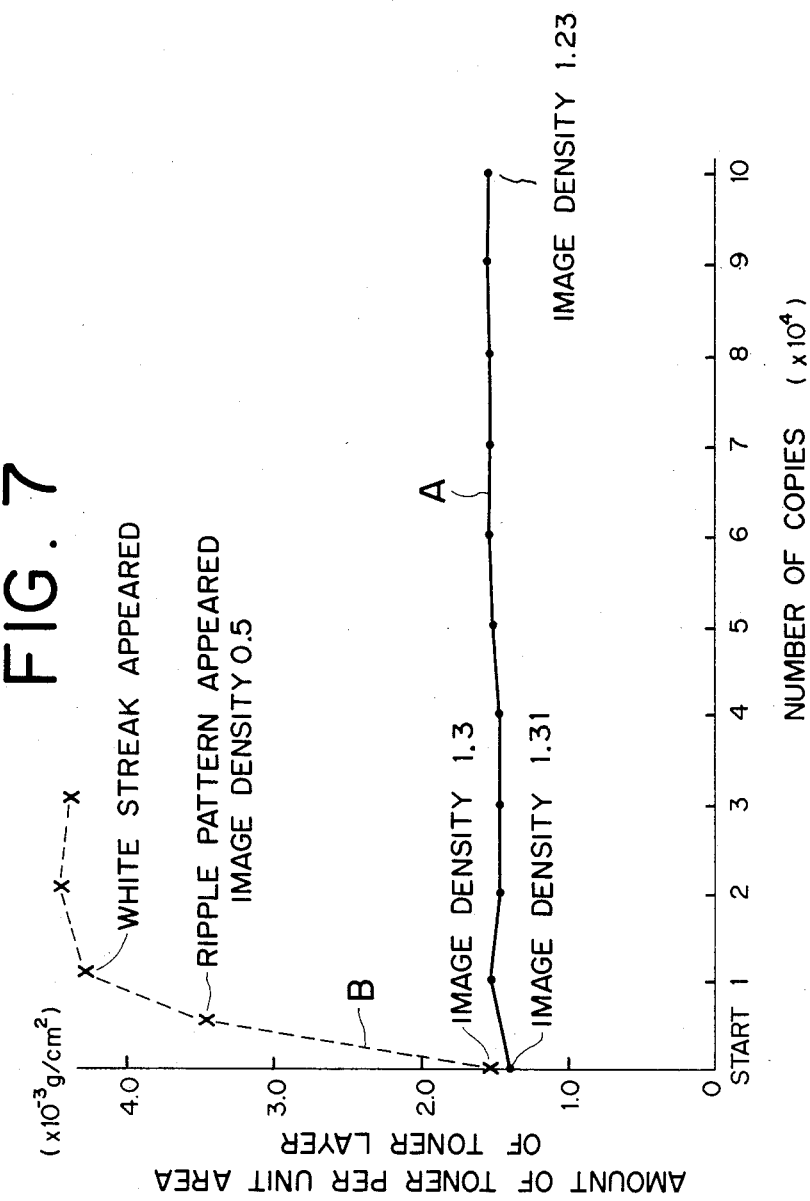

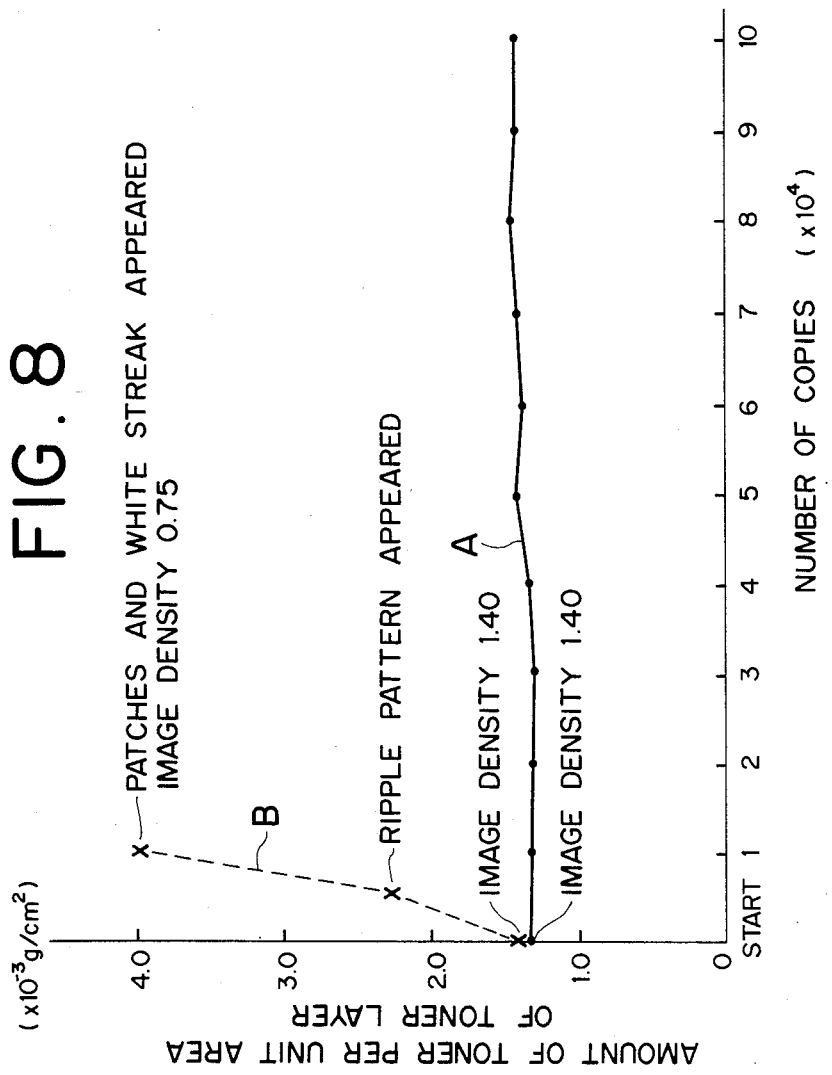

DEVELOPER AND DEVELOPING METHOD

This application is a continuation-in-part of application Ser. No. 522,501 filed Aug. 12, 1983, now abandoned.

BACKGROUND OF THE INVENTION

1. Field of the Invention

This invention relates to a developer for developing electrostatically charged images in electrostatography including electrophotography, electrostatic recording, electrostatic printing and others and also to a developing method using the same. More particularly, this invention pertains to a developer for electrophotography, which is strongly and uniformly charged to positive charges and is used for visualizing negatively charged electrostatic images to give images of high quality in the direct or indirect electrophotographic developing process, and also to an electrostatographic developing method using the same.

2. Description of the Prior Art

A large number of electrophotographic processes have been known, as disclosed in U.S. Pat. No. 2,297,691 and others. Generally speaking, photoconductive materials are utilized in these processes, and the steps included therein comprise forming electrical latent images on photosensitive members by various means, then developing the latent images by using developing powders (frequently called as "toner"), transferring the toner images thus formed to a recording medium such as paper, as desired, and thereafter fixing the images by heating, pressure or solvent vapor to obtain copies. When the step of transferring the toner images is applied, it is a general practice to provide a step for removing residual toner on the photosensitive member.

The developing metods for visualizing electrical latent images by use of toners known in the art may include, for example, the magnetic brush method as disclosed in U.S. Pat. No. 2,874,063; the cascade developing method as disclosed in U.S. Pat. No. 2,618,552; the powder cloud method as disclosed in U.S. Pat. No. 2,221,776; the method using conductive magnetic toner as disclosed in U.S. Pat. No. 3,909,258; the method using various insulating magnetic toners as disclosed in Japanese Patent Publication No. 9475/1976; and others.

As the toner for dry development system to be applied for these developing methods, use has heretofore generally been made of fine powder of natural or synthetic resins having dyes or pigments dispersed therein. For example, a colorant is dispersed in a binder resin such as polystyrene, and the particles obtained by micropulverizing the resultant dispersion into sizes of about 1 to 30$\mu$ are used as the toner. As the magnetic toner, magnetic particles are further incorporated into the particles as mentioned above. In case of the system employing the so called two-component developer, the toner as mentioned above is used generally in mixture with carrier particles such as glass beads, iron particles and others.

In a series of developing methods of electrostatographic processes as mentioned above, wherein electrostatically charged images are developed with a toner charged to the polarity opposite to that of the images, it is very important that the toner should be charged to the opposite polarity evenly in order to give good and faithful developing characteristics. For this purpose, it is generally practiced to add a positive or negative charge controller in addition to the above components in order for the toner to be charged evenly. Among such charge controllers, positive charge controllers having satisfactory characteristics are very few, while there have been developed some negative charge controllers having good characteristics.

Positive charge controllers conventionally used in toners for dry development system, may include, for example, amino compounds, quaternary ammonium compounds and organic dyes, particularly basic dyes and salts thereof. More specifically, benzyldimethylhexadecylammonium chloride, decyl-trimethylammonium chloride, nigrosine base, nigrosin hydrochloride, safranine $\gamma$, crystal violet and others are known. Particularly, nigrosine base and nigrosine hydrochloride have been frequently used as positive charge controllers. These dyes are usually added to a thermoplastic resin together with a colorant in the course of formation of a toner to be dispersed in the resin while it is molten under heating, and the resultant resin mixture is micropulverized into fine particles, adjusted to suitable sizes, if desired, and then provided for use as a toner.

However, these dyes as charge controllers have complicated structures and do not have constant properties, thus being poor in stability. Also, decomposition or denaturation may occur through decomposition, mechanical collision and friction during kneading under heat or change in temperature and humidity conditions, to cause lowering in the charge controlling characteristic.

Accordingly, when development is carried out by use of a toner containing these dyes as charge controllers in a copying machine, the dyes may undergo decomposition or denaturation as the increase in number of copies to cause deterioration of the toner during continual use.

As another serious disadvantage, it is very difficult to disperse these dyes as charge controllers evenly into a thermoplastic resin, and their contents in toner particles obtained by pulverization are not constant to result in different amounts of triboelectric charges among the toner particles. For this reason, in the prior art, various methods have been practiced in order to disperse these dyes more evenly into a resin. For example, a basic nigrosine dye is formed into a salt with a higher fatty acid for improvement of compatibility with a thermoplastic resin. In this case, however, unreacted fatty acid or decomposed product of the salt will be exposed on the toner surfaces to contaminate carriers or toner carrying member and also cause lowering in free flowing properly of the toner, fog and lowering in image density. Alternatively, for improvement in dispersibility of these dyes into a resin, there is also employed a method in which dye powders and resin powders are previously mechanically pulverized and mixed before fusion kneading. This method is not competent enough to overcome the original poor dispersibility, and evenness of charging satisfactory in practical application has not yet been obtained.

Most of dyes for positive charge controlling are hydrophilic and therefore, due to poor dispersibility of these dyes into a resin, the dyes are exposed on the toner surfaces when pulverized after fusion kneading. When the toner is used under highly humid conditions, a drawback that no image of good quality can be obtained, is encountered because of hydrophilic nature of the dye.

Thus, when a dye having positive charge controlling characteristic of the prior art is used in a toner, variances in amount of the charges generated on the toner particle surfaces through friction among toner particles, between toners and carriers or between toners and toner carrying member such as sleeve, will occur, whereby various inconveniences are caused, such as development fog, toner scattering, carrier contamination, etc. These difficulties become marked when a large number of copying cycles were carried out continuously, giving the results essentially unsuitable for a copying machine.

Also, when the toner containing a positive charge controlling dye is used, the transfer efficiency of the toner image is markedly lowered under highly humid conditions to be unsuitable for practical use. Even under normal temperature and humidity, when the toner is stored for a long time, due to instability of the positive charge controlling dye employed, toner particles may frequently agglomerate to become useless.

As a method for obtaining a positive charge controlling developer, there is a proposal as disclosed in Japanese Patent Publication No. 22447/1978. This is a method in which metal oxide particles treated with aminosilanes are incorporated as a constituent of the developer. However, as the result of my investigation on this method, when developers were obtained according to the examples disclosed in the Japanese Patent by applying treatments on metal oxides such as colloidal silica, alumina, titanium dioxide, zinc oxide, iron oxide, γ-ferrite, magnesium oxide, etc., no developer exhibiting satisfactory characteristics in practical application could be obtained in any of the combinations, but such a developer was found to have some drawbacks.

Thus, most of the developers thus prepared cannot maintain the preferable characteristics for faithful reproduction of latent images. Although desirable performance may be exhibited at the initial stage, it cannot be maintained in continuous use for a long term to make the developer useless. More specifically, fog is formed with scattering of the toner around the edges in copying of line images, and the image density is also lowered.

As other drawbacks, when developing and transfer are conducted under the conditions of higher temperature and humidity, and lower temperature and humidity, lowering in image density, scattering of line images, drop-off of images, fog, etc., are encountered. These phenomena are observed in both developing step and transfer step.

As still another drawback, the developer cannot be stored for a long term. Thus, when the developer is placed under non-used state for a long time, the characteristics at the initial stage are lowered so that the developer is no longer useful.

Various causes for these drawbacks may be thought of, but, as the result of my studies about the above phenomena, the primary cause was found to be that the distribution in amount of the triboelectric charges of the thus obtained developer was broad and not uniform. In connection with this point, a slightly detailed explanation is given below.

According to the developing methods known in the art, the forces applied on the developer particles are electrostatic attracting force toward latent image and, sometimes electrical forces from outside, image force toward the carriers or the toner carrying member such as a developing sleeve, and adhering or agglomerating forces, and adhesion of the developer particles to the latent image is effected through the total contribution of these forces. Accordingly, the state of triboelectric charge assumed by the developer particles will have important effects on the behaviors of the developer particles during the developing step. On the other hand, the developer containing metal oxide powders such as fine silica powders treated only with an aminosilane compound as described above, cannot maintain in most cases its preferable characteristics for faithful reproduction of latent images, and the distribution in amount of triboelectric charges of the developer becomes very broad. The above mentioned distribution in amount of triboelectric charges is also broad, even when the kind or the amount of the aminosilane compound used for treatment of fine silica powders may be varied, only to give a developer which includes components having smaller triboelectric charges and components having extremely great triboelectric charges after friction with carriers or a toner carrying member such as a developing sleeve. There also exist a slight quantity of components charged to opposite polarity with a greater value. (see Comparative Example 2A and FIG. 3(a), shown below)

In such a developer having a broad distribution of triboelectric charges, the developer components with smaller charge may cause fog or scattering at the edge portion of the latent image, and similar effects may also be incurredby the components charged to opposite polarity. On the other hand, the developer components with greater charge may be affected by increased image force applied from carriers or a toner carrying member such as developing sleeve may not be readily used for developing, whereby lowering of image density or coarsening may undesirably be caused.

The distribution in amount of triboelectric charges of such a developer containing fine silica powder treated only with an aminosilane compound is also susceptible to changes in environmental conditions and will become a distribution unsuitable for development particularly at higher temperature and humidity conditions and lower temperature and humidity conditions. Thus, at higher temperature and humidity, the developer components with smaller charge increase (see Comparative Example 2A, FIG. 3(b)) to cause further markedly fog, lowering of image density, scattering at the edge portion of latent image and lowering of transfer efficiency.

At lower temperature and humidity, the developer components with greater charge increase (see Comparative Example 2A, FIG. 3(c)) to cause more markedly lowering of image density, coarsening and fog and result in increased scattering or drop-off during transfer. Particularly at lower temperature and humidity conditions, this tendency will become further marked by continuous use of the developer, and the initial characteristics of the developer cannot be maintained until the developer becomes no longer useful.

The distribution of triboelectric charges herein mentioned refers to a charged quantity to be measured under the state approximate to the developing system employed. For example, in the two-component developing method, the cascade developing system or the two-component magnetic brush system, charging of the developer particles is effected primarily in the step of contacting with or peeling off from the carrier particle surfaces. Measurement of the distribution in amount of triboelectric charges in such developer systems may be conducted by use of, for example, the method of L. B. Schein et al (J. Appl. Phys. 46, No. 12, P. 5140 (1975)), or the method of R. W. Stover et al (1969 Proc. Ann. Conf. Photo. Sci. Engy SPSE P. 156) and R. B. Levis et al (4th International Conf. on Electrophoto. Adv. Print P. 61 (1981)).

SUMMARY OF THE INVENTION

An object of the present invention is to provide a developer which is stable in amount of triboelectric charges caused between toner particles, or between toner and carrier, or between toner and a toner carrying member such as a sleeve in case of one-component development, also sharp and even in distribution in amount of triboelectric charges, and can be controlled to a charged amount suitable for the developing system employed.

Another object of the present invention is to provide a developer capable of permitting development and transfer to be effected faithfully to latent image, that is, capable of providing a high image density with good reproducibility of half tone, without adhesion of the toner in the background region during development, namely, without fog or scattering of toner around the edge of latent image.

Still another object of the present invention is to provide a developer, which can maintain the initial characteristics and is free from agglomeration of toners or changes in charging characteristics, even when the developer is used continuously for a long term.

Further object of the present invention is to provide a developer capable of reproducing stable images without suffering from influences from temperature and humidity, particularly with high transfer efficiency, being free from scattering or transfer failure, i.e., drop-off of images, during transfer at higher humidity and lower humidity conditions.

Further, it is also another object of the present invention to provide a developer excellent in storage stability which can maintain the initial characteristics even after storage over a long term.

Still another object of the present invention is to provide a developing method adapted for repeated copying operations such as continuous operations by use of a developer as mentioned above.

Further, still another object of the present invention is to provide a developing method which is stable even against environmental changes such as under higher temperature and humidity conditions or lower temperature and humidity conditions.

I have studied intensively with an aim to provide a developer for electrostatography, particularly for electrophotography, which is positively chargeable developer capable of being strongly and evenly charged positively and giving an image of high quality through visualization of a negatively charged electrostatic image, by overcoming various problems involved in the positively charged toner of the prior art as described above. As a consequence, the developer of the present invention has been attained.

The developer according to the present invention comprises a binder resin, a colorant and a positive charge controller, the positive charge controller comprising fumed silica particles treated with a coupling agent having a hydrolyzable group and a non-hydrolyzable organic group bonded to a tetravalent center atom of Si or Ti and having a hydrophobicity within the range of from 30 to 80 as measured by the methanol titration test.

The developing method according to the present invention employs the above developer which is made insulating and magnetic, and comprises providing an electrostatic image bearing member for bearing electrostatic images on its surface and a developer carrying member arranged with a predetermined gap therebetween, permitting the insulating magnetic developer to be carried on the developer carrying member in a thickness thinner than the gap, and transferring the developer to the electrostatic image bearing member thereby to develop the electrostatic images.

Examples of adding fine fumed silica powder to a developer for electrophotography are known in the art. However, even a developer containing a dye having positive charge controlling characteristic is changed to negative in its charging polarity and therefore unsuitable for visualization of negative electrostatic images. This is because fine fumed silica powder will reduce the charges of the positively charged developer or even reverse the charging polarity.

Whereas, I have found that an excellent positive charge controller can be obtained by treating such fumed silica powder with a silane or a titanate type coupling agent and controlling the hydrophobicity to an appropriate level, and that a positively chargeable developer which is stably charged to have high triboelectric charges with sharp and uniform distribution, can be obtained by formulation of the controller in the developer. It has also been found that, by controlling both the degree of treatment with the coupling agent and the hydrophobicity, the amount of the triboelectric charge of the toner containing the resultant positive charge controller as well as its distribution can be controlled to a considerable extent.

It has not yet been clarified in detail why the developer of the present invention has sharp and uniform distribution in amount of triboelectric charges (see Example 1A and FIGS. 2(a) to (c)) (probably due to stabilization at a certain equilibrated value between the leak of excessive charges and charge accumulation through the interaction between the coupling agent and the hydrophobicity modifying agent). Anyway, it has been confirmed that there are few components in the developer having deleterious influences on development and transfer, and the distribution and of triboelectric charges are little changed even under the conditions of higher temperature and humidity or lower temperature and humidity.

BRIEF DESCRIPTION OF THE DRAWINGS

FIG. 5 to FIG. 8 are graphs each showing toner weight changes per unit area in the toner layers during successive copying test under the environment of 10° C. and 10% R.H., A showing the results of an Example and B that of a Comparative Example in each case. The respective Figures show the results of the following examples.

FIG. 5: Example 1F, Comparative Example 3F;
FIG. 6: Example 1G, Comparative Example 3G;
FIG. 7: Example 1H, Comparative Example 3H;
FIG. 8: Example 1I, Comparative Example 3I.

DESCRIPTION OF THE PREFERRED EMBODIMENTS

In the following description, "%" and "parts" representing quantity ratios are all based on weight, unless otherwise indicated.

The specific positive charge controller to be used in the developer of the present invention is obtained from fumed silica. "Fumed silica" used herein refers comprehensively to fine silica powder obtained by vapor phase oxidation of silicon halides, and may also sometimes called as the dry process silica. The method for preparation of fumed silica is known in the art, and it can be obtained, for example, by pyrolytic oxidation of gaseous silicon tetrachloride in oxygen-hydrogen flame. The basic reaction scheme may be represented as follows:

$$SiCl_4 + 2H_2 + O_2 \rightarrow SiO_2 + 4HCl$$

In the above preparation step, it is also possible to obtain complex fine powder of silica and other metal oxides by using other metal halides such as aluminum chloride or titanium chloride together with silicon halides. Thus, in the present specification, "fumed silica" is meant to be inclusive of silica containing metal oxides such as $Al_2O_3$, $TiO_2$, etc. derived from these metal halides up to 40%.

It is preferred to use fumed silica particles, of which mean primary particle size is desirably within the range of from 0.001 to $2\mu$, particularly preferably of from 0.002 to $0.2\mu$.

Commercially available fumed silica products to be used in the present invention include those sold under the trade names as shown below.

| | |
|---|---|
| AEROSIL | 130 |
| (Nippon Aerosil Co.) | 200 |
| | 300 |
| | 380 |
| | TT 600 |
| | MOX 80 |
| | COK 84 |
| Ca-O-Sil | M-5 |
| (Cabot Co.) | MS-7 |
| | MS-75 |
| | HS-5 |
| | EH-5 |
| Wacker HDK N 20 | V 15 |
| (WACKER-CHEMIE GMBH) | N 20E |
| | T 30 |
| | T 40 |
| D-C Fine Silica | |
| (Dow Corning Co.) | |
| Fransol | |
| (Fransil Co.) | |

Figure 4A:
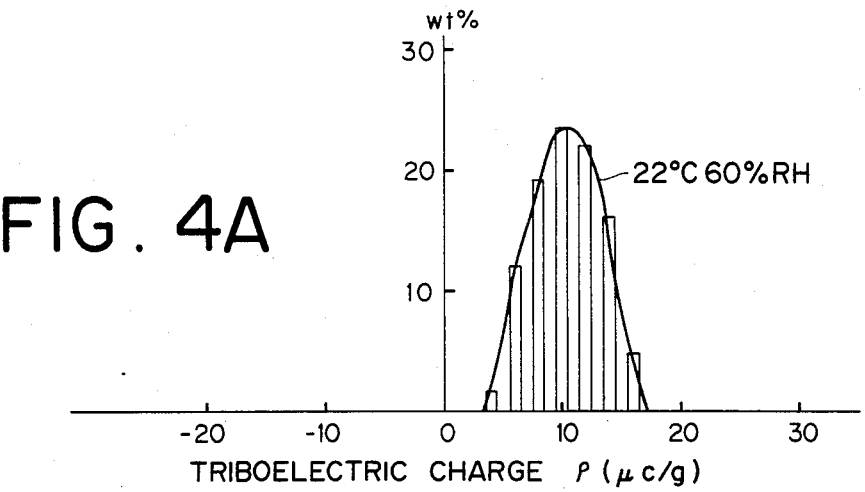
Figure 4B:
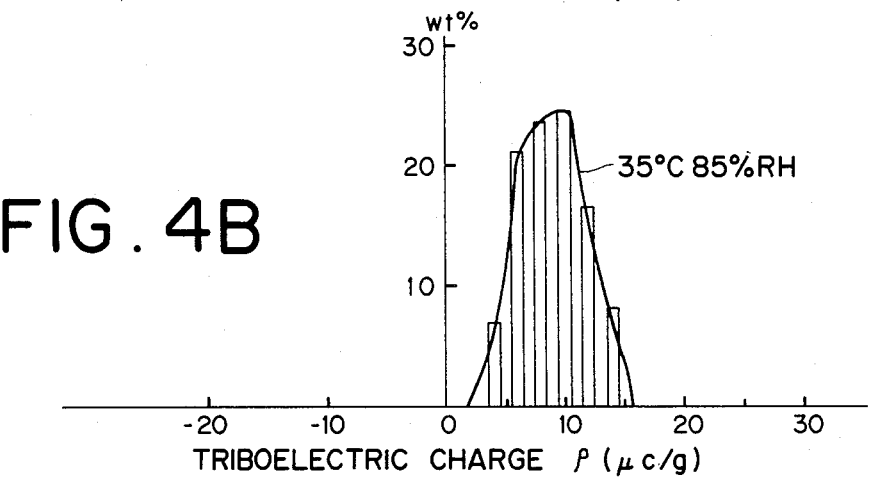
Figure 4C:
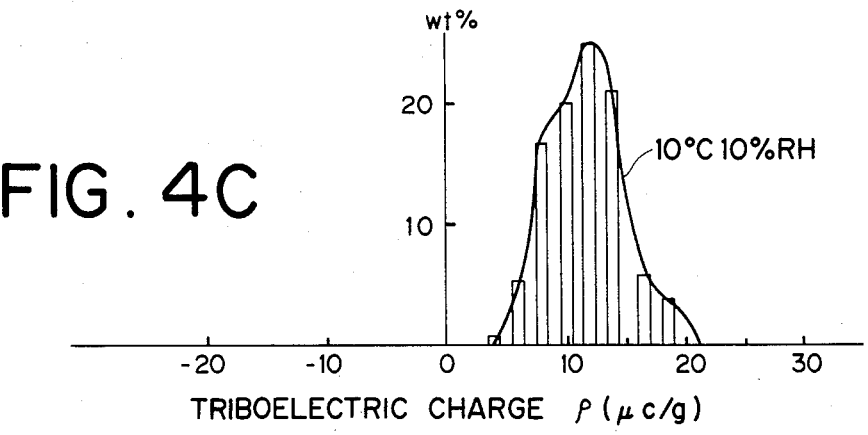

These fumed silica particles may be used as such. More preferably, however, they are subjected once to heat treatment at a temperature of 400° C. or higher before subsequent treatment with a coupling agent. By effecting this heat treatment, there can be obtained additional effects that not only the components of the developer obtained having deleterious influences on development and transfer can be removed to further make shaper the distribution in amount of triboelectric charges (see Example 1B and FIGS. 4(a) to (c) shown below), but also the reduction in amount of triboelectric charges is very small without substantial lowering in quality of copying even if the developer is stored for a long term under the conditions of high temperature and high humidity. This may be attributable to the following reason. That is, fumed silica, namely, fine silica particles formed by vapor phase oxidation of a silicon halide compound, have a large number of hydroxyl groups formed on their surfaces. These hydroxyl groups may be classified into the several kinds as mentioned below.

1. Silanol groups on the surfaces: these groups have no possibility of mutual interaction within their acting regions, because they are spacially made apart from other silanol groups, and therefore called as "lone" or "free" silanol groups;

2. The same kind of groups per se as 1 above, with proviso that these groups are approximated so as to be capable of interaction through hydrogen crosslinking, and therefore may be called as "bonded (hydrogen crosslinked) silanol groups";

3. Hydroxyl groups of water adsorbed on the surfaces.

When fumed silica particles are subjected to the heat treatment at 400° C. or higher, condensation will occur mutually between the silanol groups among these hydroxyl groups on the silica surfaces, to result in stabilization of the surface. When heat treated at a temperature below 400° C., the adsorbed water is removed to reduce the water content in the fumed silica, but when returned to normal temperature, it absorbs again water to a water content equal to that before heat treatment. However, when treated at a temperature of 400° C. or higher, water is liberated through condensation of the hydroxyl groups on the surface, and therefore the water content becomes markedly smaller as compared with that before the heat treatment, even when returned to normal temperature. Although the hydroxyl groups cannot completely be removed, the residual number of hydroxyl groups is convenient for hydrophobicity modification treatment which is to be effected as the post-treatment, if desired.

The heat treatment may be conducted by, for example, leaving fine silica powder to stand in an electric furnace at a temperature of 400° C. or higher for a suitable length of time. So far as the characteristics of the developer are not markedly lowered, the heat treatment method is not particularly limited, but any desirable method can be employed. The heat treatment temperature may be preferably 450° C. to 1500° C., particularly 500° C. to 1000° C.

The time for the heat treatment may vary depending on the treatment temperature, the sizes of the fumed silica particles and other characteristics, but generally range from one minute to 10 hours, particularly from 10 minutes to 10 hours, which can be determined with a measure that the hygroscopicity as the result of the heat treatment may become 5% or below (particularly 3% or below). The hygroscopicity is measured by subjecting the heat-treated fumed silica particles to standing on a saturated aqueous solution with sodium thiosulfate at the bottom, i.e. in a humidity of 78%, for about one week and thereafter to measurement of the heating reduction curve from normal temperature to 400° C. by means of a thermobalance, and determining its reduced quantity as the hydroscopicity.

For obtaining the developer of the present invention, the fumed silica, optionally subjected to the heat treatment as described above, is treated with a coupling agent. The coupling agent used herein comprises a silane type or titanate type coupling agent, having a hydrolyzable group and a non-hydrolyzable organic group bonded to the tetravalent center atom of Si or Ti.

For example, the silane type coupling agent may include those represented by the formula (1) shown below:

$$R_m SiY_n \qquad (1)$$

wherein R is an alkoxy group having 1 to 10 carbon atoms such as methoxy, ethoxy, propoxy, isopropoxy, butoxy, isobutoxy, pentyloxy and the like groups, or a chlorine atom; m and n are integers satisfying the relation of m+n=4; Y is an organic group containing at least one of amino, vinyl, glycidoxy, mercapto, methacryl, and ureido groups, particularly a hydrocarbyl group in which a part of the hydrogen atoms can be further substituted with a carbonyl, ether, ester or imino group; with proviso that a plurality of R and Y existing in the same compound may be the same or different.

Typical examples of the coupling agents of the formula (1) are enumerated below.

Compounds having vinyl group:
H$_2$C=CHSiCl$_3$
H$_2$C=CHSi(OC$_2$H$_5$)$_3$
H$_2$C=CHCH$_2$SiCl$_3$
H$_2$C=CHCH$_2$Si(CH$_3$)Cl$_2$
H$_2$C=CHCH$_2$Si(CH$_3$)$_2$Cl
H$_2$C=CHCH$_2$Si(OC$_2$H$_5$)$_3$
H$_2$C=CHSi(OC$_2$H$_4$OCH$_3$)$_3$
(H$_2$C=CHCH$_2$)$_2$SiCl$_2$
(H$_2$C=CH)$_2$Si(OC$_2$H$_5$)$_2$
(H$_2$C=CH)$_3$SiOC$_2$H$_5$

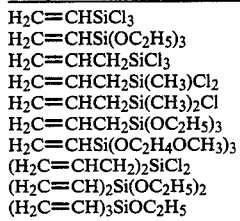

Compounds having glicidoxy group:

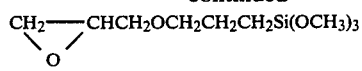

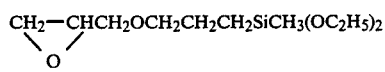

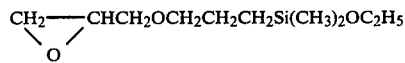

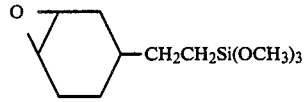

Compounds having mercapto group:
HSCH$_2$CH$_2$CH$_2$Si(OCH$_3$)$_3$
HSCH$_2$CH$_2$CH$_2$Si(OC$_2$H$_5$)$_3$
Compounds having methacryl group:

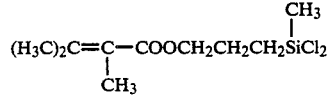

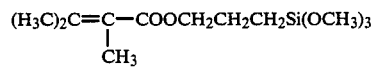

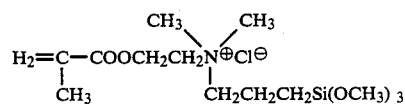

Compounds having ureido group:
H$_2$NCONHCH$_2$CH$_2$CH$_2$Si(OC$_2$H$_5$)$_3$

In particular, preferable silane coupling agents to be used in the present invention are compounds having an amino group, examples of which are those having the structural formulas as shown below:

H$_2$NCH$_2$CH$_2$CH$_2$Si(OCH$_3$)$_3$
H$_2$NCH$_2$CH$_2$CH$_2$Si(OC$_2$H$_5$)$_3$

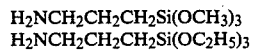

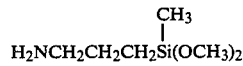

H$_2$NCONHCH$_2$CH$_2$CH$_2$Si(OC$_2$H$_5$)$_3$
H$_2$NCH$_2$CH$_2$NHCH$_2$CH$_2$CH$_2$Si(OCH$_3$)$_3$
H$_2$NCH$_2$CH$_2$NHCH$_2$CH$_2$NHCH$_2$CH$_2$CH$_2$Si(OCH$_3$)$_3$
H$_5$C$_2$OCOCH$_2$CH$_2$NHCH$_2$CH$_2$CH$_2$Si(OCH$_3$)$_3$
H$_5$C$_2$OCOCH$_2$CH$_2$NHCH$_2$CH$_2$NHCH$_2$CH$_2$CH$_2$Si(OCH$_3$)$_3$
H$_5$C$_2$OCOCH$_2$CH$_2$NHCH$_2$CH$_2$NHCH$_2$CH$_2$NHCH$_2$CH$_2$CH$_2$Si(OCH$_3$)$_3$
H$_3$COCOCH$_2$CH$_2$NHCH$_2$CH$_2$NHCH$_2$CH$_2$CH$_2$Si(OCH$_3$)$_3$

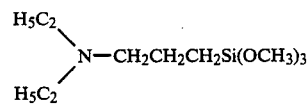

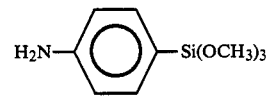

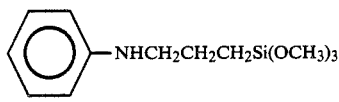

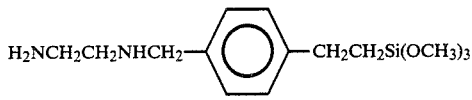

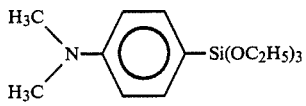

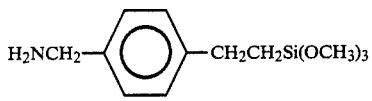

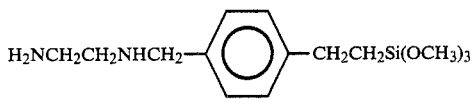

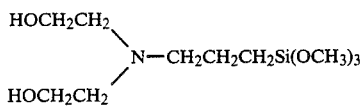

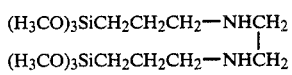

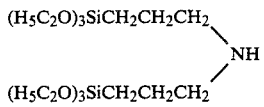

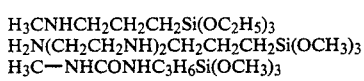

H₃CNHCH₂CH₂CH₂Si(OC₂H₅)₃
H₂N(CH₂CH₂NH)₂CH₂CH₂CH₂Si(OCH₃)₃
H₃C—NHCONHC₃H₆Si(OCH₃)₃

In the above compounds, the alkoxy group may be replaced by chlorine atoms.

As another group of silane type coupling agents, there are cation type unsaturated amino-functional silanes represented by the formula (2) shown below:

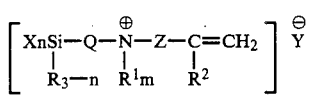

wherein X is a hydroxyl group or a hydrolyzable group; R is an alkyl having 1 to 6 carbon atoms; n is an integer of 1 to 3; Q is a divalent hydrocarbon group, or an organic group containing oxygen in the form of

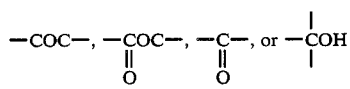

or nitrogen in the form of R²N= group, the rest, if any, of the organic group comprising a hydrocarbon unit in most cases; R¹ is a hydrogen atom, an alkyl group having 1 to 6 carbon atoms or a heterocyclic organic group having nitrogen atom in the ring; m is 1 or 2; Z is a divalent organic group having a double bond conjugated with

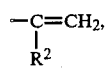

and bonded through through C—N bonding to the nitrogen atom on its left side; R² is a hydrogen atom or an alkyl having 1 to 6 carbon atoms; and Y is an acid anion.

More particularly, X is a hydroxyl group or a hydrolyzable group such as alkoxy group, aryloxy group, hydrogen atom, acyloxy group, ketooxime group, amino group, etc. The "hydrolyzable group" herein mentioned means a group which can react with water at room temperature to form a silanol.

R is a lower alkyl having not more than 6 carbon atoms. The R groups bonded to the same silicon atom may be the same or different.

The binding group Q between the silicon atom and the nitrogen atom is constituted of carbon, hydrogen, oxygen or nitrogen, containing oxygen in the form of carbonyl, ether, ester or hydroxyl or containing nitrogen in the form of amide.

Specific examples of Q are divalent hydrocarbon groups, carbonyl groups, ether groups, ester groups or a group having a hydroxyl group as shown below:

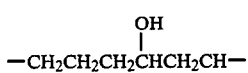

Alternatively, Q may also contain nitrogen as shown below:

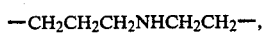

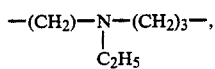

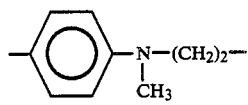

$R^1$ is selected independently from the groups such as hydrogen atom, alkyl groups similar to R and heterocyclic groups having nitrogen in the ring as shown below:

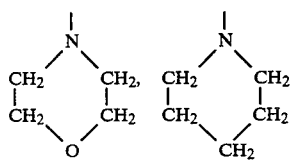

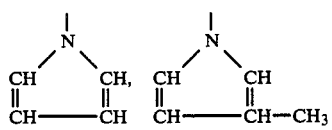

of course, when $R^1$ is such a heterocyclic group, m is 1, but when $R^1$ is hydrogen or a lower alkyl, m is 2.

Z is a divalent organic group constituted of carbon, hydrogen and oxygen as mentioned in connection with the group Q, and is further characterized by having a double bond conjugated with a vinyl group. Z is bonded through carbon-nitrogen bonding to the nitrogen group on its left side. Examples of such divalent groups are arylene group, carbonyl group and vinyl group.

$R^2$ is a hydrogen atom or an alkyl having 1 to 6 carbon atoms.

Y is a hydrogen atom; chlorine, bromine, iodine; or an acidic anion such as carboxylate anion, or, for example, formate anion, aceatate anion, phosphate anion, sulfate anion, nitrate anion, etc.

Typical examples of the compounds represented by the above formula (2) are enumerated below. These compounds can be prepared by the reaction between amino functional silanes and conjugated unsaturated alkyl halides. Alternatively, they can also be prepared by the reaction between silicon alkyl halides and conjugated unsaturated aliphatic amines.

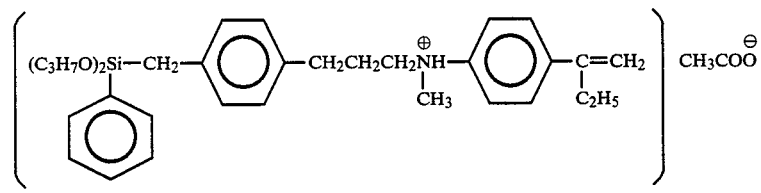

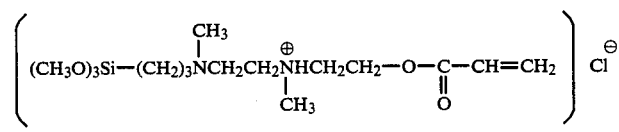

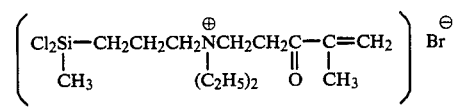

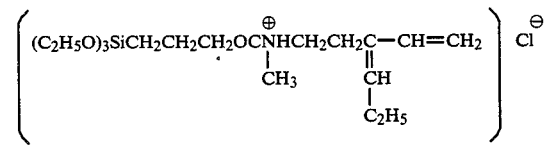

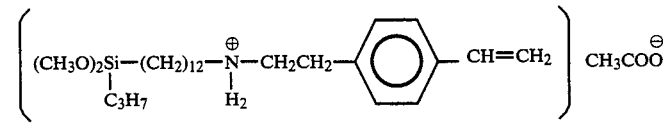

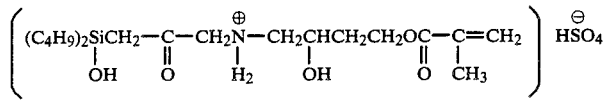

The above cation type unsaturated amino-functional silane can be also used as its hydrolyzate for treatment of fumed silica.

Examples of the titanate type coupling agent include the compounds represented by the following formula:

$$R_m\text{—Ti—}X_n \qquad (3)$$

wherein m and n are 1 and 2, 1 and 3 or 4 and 2, respectively; R is preferably an alkoxy having 1 to 10 carbon atoms such such as methoxy, ethoxy, propoxy, iropropoxy, butoxy, isobutoxy, pentyloxy, etc. or

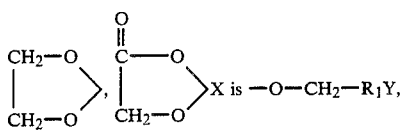

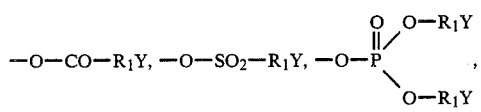

-continued

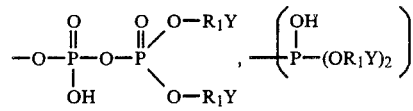

(in the above formulae, $R_1$ is a saturated or unsaturated divalent aliphatic group having 1 to 34 carbon atoms such as

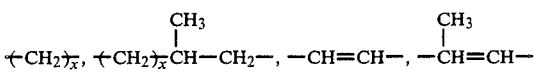

where x is an integer of 1 to 31, or a divalent aromatic hydrocarbylene group; Y is a hydrogen atom or an amino group; and a plurality of X, $R_1$ and Y existing in the same compound being the same or different, respectively).

Typical examples of the titanate type coupling agents may include those as enumerated below:

| Chemical Name | Chemical structure |
|---|---|
| Isopropyl tristearoyl | CH₃—CH(CH₃)—O—Ti(—O—C(=O)—C₁₇H₃₅)₃ |
| Isopropyl trioctanoyl titanate | CH₃—CH(CH₃)—O—Ti(—O—C(=O)—C₇H₁₅)₃ |
| Isopropyl diisostearoyl cumylphenyl titanate | CH₃—CH(CH₃)—O—Ti with (—O—C(=O)—C₁₇H₃₅)₂ and —O—C₆H₄—C(CH₃)₂—C₆H₅ |
| Isopropyl distearoyl methacryl titanate | CH₃—CH(CH₃)—O—Ti with (—O—C(=O)—C₁₇H₃₅)₂ and —O—C(=O)—C(CH₃)=CH₂ |

-continued

| Chemical Name | Chemical structure |
|---|---|
| Isopropyl dimethacryl isostearoyl titanate | $\text{CH}_3-\text{CH}(\text{CH}_3)-\text{O}-\text{Ti}(-\text{O}-\overset{\text{O}}{\underset{\|}{\text{C}}}-\text{C}_{17}\text{H}_{35})(-\text{O}-\underset{\overset{\|}{\text{O}}}{\text{C}}-\underset{\text{CH}_3}{\text{C}}=\text{CH}_2)_2$ |
| Isopropyl tridodecylbenzene sulfonyl titanate | $\text{CH}_3-\text{CH}(\text{CH}_3)-\text{O}-\text{Ti}{-}\!\left(\text{O}-\overset{\text{O}}{\underset{\overset{\|}{\text{O}}}{\text{S}}}-\text{C}_6\text{H}_4-\text{C}_{12}\text{H}_{25}\right)_3$ |
| Isopropyl diisostearoyl acryl titanate | $\text{CH}_3-\text{CH}(\text{CH}_3)-\text{O}-\text{Ti}(-\text{O}-\overset{\text{O}}{\underset{\|}{\text{C}}}-\text{C}_{17}\text{H}_{35})_2(-\text{O}-\underset{\overset{\|}{\text{O}}}{\text{C}}-\text{CH}=\text{CH}_2)$ |
| Isopropyl diisostearoyl diacryl titanate | $\text{CH}_3-\text{CH}(\text{CH}_3)-\text{O}-\text{Ti}(-\text{O}-\overset{\text{O}}{\underset{\|}{\text{C}}}-\text{C}_{17}\text{H}_{35})(-\text{O}-\underset{\overset{\|}{\text{O}}}{\text{C}}-\text{CH}=\text{CH}_2)_2$ |
| Isopropyl tri(dioctylphosphate) titanate | $\text{CH}_3\text{CH}(\text{CH}_3)-\text{O}-\text{Ti}{-}\!\left(\text{O}-\overset{\text{O}}{\underset{\|}{\text{P}}}(\text{O}-\text{C}_8\text{H}_{17})_2\right)_3$ |
| Isopropyl tri-n-stearoyl titanate | $\text{CH}_3-\text{CH}(\text{CH}_3)-\text{O}-\text{Ti}{-}\!\left(\text{O}-\overset{\text{O}}{\underset{\|}{\text{C}}}-\text{C}_{17}\text{H}_{35}\right)_3$ |
| Isopropyl 4-aminobenzene sulfonyl di(dodecylbenzenesulfonyl) titanate | $\text{CH}_3-\text{CH}(\text{CH}_3)-\text{O}-\text{Ti}(-\text{O}-\overset{\text{O}}{\underset{\overset{\|}{\text{O}}}{\text{S}}}-\text{C}_6\text{H}_4-\text{NH}_2)(-\text{O}-\overset{\text{O}}{\underset{\overset{\|}{\text{O}}}{\text{S}}}-\text{C}_6\text{H}_4-\text{C}_{12}\text{H}_{25})_2$ |
| Isopropyl trimethacryl titanate | $\text{CH}_3-\text{CH}(\text{CH}_3)-\text{O}-\text{Ti}{-}\!\left(\text{O}-\overset{\text{O}}{\underset{\|}{\text{C}}}-\underset{\text{CH}_3}{\text{C}}=\text{CH}_2\right)_3$ |
| Isopropyl tricumylphenyl titanate | $\text{CH}_3-\text{CH}(\text{CH}_3)-\text{O}-\text{Ti}{-}\!\left(\text{O}-\text{C}_6\text{H}_4-\text{C}(\text{CH}_3)_2-\text{C}_6\text{H}_5\right)_3$ |

-continued

| Chemical Name | Chemical structure |
|---|---|
| Isopropyl di(4-aminobenzoyl) isostearoyl titanate | $CH_3-CH(CH_3)-O-Ti\left[-O-C(=O)-C_6H_4-NH_2\right]_2 \cdot [-O-C(=O)-C_{17}H_{35}]$ |
| Isopropyl tri(dioctylpyrophosphate) titanate | $CH_3-CH(CH_3)-O-Ti\left[-O-P(=O)(OH)-O-P(=O)(O-C_8H_{17})_2\right]_3$ |
| Isopropyl triacryl titanate | $CH_3-CH(CH_3)-O-Ti\left[-O-C(=O)-CH=CH_2\right]_3$ |
| Isopropyl tri(N,N—dimethylethylamino) titanate | $CH_3-CH(CH_3)-O-Ti\left[-O-CH_2-CH_2-N(CH_3)_2\right]_3$ |
| Isopropyl tri(N—ethyl-aminoethylamino) titanate | $CH_3-CH(CH_3)-O-Ti(-O-C_2H_4-NH-C_2H_4-NH_2)_3$ |
| Isopropyl trianthranyl titanate | $CH_3-CH(CH_3)-O-Ti\left[-O-C(=O)-C_6H_4-NH_2\right]_3$ |
| Isopropyl octyl, butyl pyrophosphate titanate | $CH_3-CH(CH_3)-O-Ti\left[-O-P(=O)(OH)-O-P(=O)(O-C_8H_{17})(O-C_4H_9)\right]_3$ |
| Isopropyl di(butyl, methyl pyrophosphate) titanate | $CH_3-CH(CH_3)-O-Ti\left[-O-P(=O)(OH)-O-P(=O)(O-C_4H_9)(O-CH_3)\right]_3$ |
| Tetraisopropyl di(laurylphosphite)titanate | $\left(CH_3-CH(CH_3)-O\right)_4 Ti \cdot (P(-O-C_{12}H_{25})_2OH)_2$ |
| Tetraisopropyl di(octylphosphite)titanate | $\left(CH_3-CH(CH_3)-O\right)_4 Ti \cdot (P(-O-C_8H_{17})_2OH)_2$ |
| Tetraoctyl di(tridecylphosphite)titanate | $(C_8H_{17}-O)_4 Ti \cdot (P(-O-C_{13}H_{27})_2OH)_2$ |
| Tetra(2,2-diallyloxymethyl-1-butoxy)-di-(di-tridecyl)-phosphite titanate | $\left(C_2H_5-C(-(CH_2-O-CH-CH=CH_2)_2)-CH_2O-\right)_4 Ti \cdot (P-(O-C_{13}H_{27})_2OH)_2$ |

| Chemical Name | Chemical structure |
|---|---|
| Diisostearoyl oxyacetate titanate | $\underset{CH_2-O}{\overset{O=C-O}{|}}\!\!\diagdown\!\!Ti\!\!\diagup\!\!\!-\!\!\left(O-\overset{O}{\underset{\|}{C}}-C_{17}H_{35}\right)_2$ |
| Isostearoyl methacryl oxyacetate titanate | $\underset{CH_2-O}{\overset{O=C-O}{|}}\!\!\diagdown\!\!Ti\!\!\diagup\!\!\!\begin{array}{l}O-\overset{O}{\underset{\|}{C}}-C_{17}H_{35}\\O-\underset{\underset{O}{\|}}{C}-\underset{CH_3}{\overset{|}{C}}=CH_2\end{array}$ |
| Isostearoyl acryl oxyacetate titanate | $\underset{CH_2-O}{\overset{O=C-O}{|}}\!\!\diagdown\!\!Ti\!\!\diagup\!\!\!\begin{array}{l}O-\overset{O}{\underset{\|}{C}}-C_{17}H_{35}\\O-\underset{\underset{O}{\|}}{C}-CH=CH_2\end{array}$ |
| Di(dioctylphosphate)-oxyacetate titanate | $\underset{CH_2-O}{\overset{O=C-O}{|}}\!\!\diagdown\!\!Ti\!\!\diagup\!\!\!-\!\!\left(O-\overset{O}{\underset{\|}{P}}\!\!-\!\!(O-C_8H_{17})_2\right)_2$ |
| 4-Aminobenzenesulfonyl-dodecylbenzenesulfonyl-oxyacetate titanate | $\underset{CH_2-O}{\overset{O=C-O}{|}}\!\!\diagdown\!\!Ti\!\!\diagup\!\!\!\begin{array}{l}O-\underset{\underset{O}{\|}}{\overset{\overset{O}{\|}}{S}}-\!\!\!\!\!\bigcirc\!\!\!\!\!-NH_2\\O-\underset{\underset{O}{\|}}{\overset{\overset{O}{\|}}{S}}-\!\!\!\!\!\bigcirc\!\!\!\!\!-C_{12}H_{25}\end{array}$ |
| Dimethacryl oxyacetate titanate | $\underset{CH_2-O}{\overset{O=C-O}{|}}\!\!\diagdown\!\!Ti\!\!\diagup\!\!\!-\!\!\left(O-\overset{O}{\underset{\|}{C}}-\underset{CH_3}{\overset{|}{C}}=CH_2\right)_2$ |
| Dicumylphenolate oxyacetate titanate | $\underset{CH_2-O}{\overset{O=C-O}{|}}\!\!\diagdown\!\!Ti\!\!\diagup\!\!\!-\!\!\left[O-\!\!\!\!\!\bigcirc\!\!\!\!\!-\underset{CH_3}{\overset{CH_3}{\overset{|}{C}}}-\!\!\!\!\!\bigcirc\right]_{(2)}$  n = 2.2 |
| 4-Aminobenzoyliso-stearoyl oxyacetate titanate | $\underset{CH_2-O}{\overset{O=C-O}{|}}\!\!\diagdown\!\!Ti\!\!\diagup\!\!\!\begin{array}{l}O-\overset{O}{\underset{\|}{C}}-\!\!\!\!\!\bigcirc\!\!\!\!\!-NH_2\\O-\underset{\underset{O}{\|}}{C}-C_{17}H_{35}\end{array}$ |
| Di(dioctylpyrophosphate)oxyacetate titanate | $\underset{CH_2-O}{\overset{O=C-O}{|}}\!\!\diagdown\!\!Ti\!\!\diagup\!\!\!-\!\!\left(O-\underset{OH}{\overset{\overset{O}{\|}}{P}}-O-\overset{O}{\underset{\|}{P}}\!\!-\!\!(O-C_8H_{17})_2\right)_2$ |

| Chemical Name | Chemical structure |
| --- | --- |
| Diacryl oxyacetate titanate | ![structure] |
| Di(octyl,butylpyrophosphate)oxyacetate titanate | ![structure] |
| Diisostearoyl ethylene titanate | ![structure] |
| Isostearoyl methacrylethylene titanate | ![structure] |
| Di(dioctylphosphate) ethylene titanate | ![structure] |
| 4-Aminobenzenesulfonyl-dodecylbenzenesulfonyl ethylene titanate | ![structure] |
| Dimethacryl ethylene titanate | ![structure] |
| 4-Aminozenzoyl isostearoyl ethylene titanate | ![structure] |
| Di(dioctylpyrophosphate) ethylene titanate | ![structure] |

-continued

| Chemical Name | Chemical structure |
|---|---|
| Diacryl ethylene titanate | $\begin{array}{c}CH_2-O\\ \phantom{CH_2-O}\diagdown\\ \phantom{CH_2-O}\diagup\\ CH_2-O\end{array}Ti\left(O-\overset{O}{\overset{\|}{C}}-CH=CH_2\right)_2$ |
| Dianthranyl ethylene titanate | $\begin{array}{c}CH_2-O\\ \phantom{CH_2-O}\diagdown\\ \phantom{CH_2-O}\diagup\\ CH_2-O\end{array}Ti\left(O-\overset{O}{\overset{\|}{C}}-C_6H_4-NH_2\right)_2$ |
| Di(butyl,methylpyrophosphate)ethylene titanate | $\begin{array}{c}CH_2-O\\ \phantom{CH_2-O}\diagdown\\ \phantom{CH_2-O}\diagup\\ CH_2-O\end{array}Ti\left(O-\overset{O}{\overset{\|}{P}}-O-\overset{O}{\overset{\|}{\underset{\|}{P}}}\underset{OH}{\phantom{X}}\begin{array}{c}O-C_4H_9\\ \diagup\\ \diagdown\\ O-CH_3\end{array}\right)_2$ |

The silane type or titanate type coupling agent as described above may be employed alone, or alternatively, two or more kinds of coupling agents selected from one or two types can be used as a mixture.

As the method for treating the fumed fine silica particles with a coupling agent, it is possible to use a wide scope of treating methods of both dry and wet methods, because the coupling agent to be used in the present invention reacts readily with the bonded water possessed chemically or physically existing on the surfaces of fine silica particles to be covered thereon. For example, into a mixing machine such as a Henschel mixer or a ball mill, fine silica particles and an appropriate amount of a coupling agent may be charged, and dry mixing is carried out. Alternatively, a coupling agent may be dissolved in a suitable solvent, and fine silica particles are charged into the resultant solution, followed by mixing, and thereafter the solvent is removed. Various other methods may also be available.

A coupling agent may be used for the treatment at a proportion of 0.01 to 20% (preferably 0.1 to 10%) based on the fine silica particles.

In order that the charge controller of the present invention can have a desired positive charging controlling characteristic, it is required to have a value of hydrophobicity within the range from 30 to 80, as measured by the methanol titration test. The "methanol titration test" defined in the present invention for evaluation of hydrophobicity is conducted as follows.

Sample fine silica particles (0.2 g) are charged into 50 ml of water in a 250 ml-Erlenmeyer's flask. Methanol is added dropwise from a buret until the whole amount of the silica is wetted therewith. During this operation, the content in the flask is constantly stirred by means of a magnetic stirrer. The end point can be observed when the total amount of the fine silica particles is suspended in the liquid, and the hydrophobicity is represented by the percentage of the methanol in the liquid mixture of water and methanol based on the quantity of methanol added on reaching the end point.

The fumed silica particles treated with a coupling agent as described above have a hydrophobicity within the range as specified above, when the coupling agent employed is a titanate type. However, when treated with a silane type coupling agent alone, the resultant particles will lack in sufficient hydrophobicity. Accordingly, in this case, the hydrophobicity is required to be controlled within the range from 30 to 80 by use of an appropriate hydrophobicity modifier. As such a method for hydrophobicity modification, there may be used any method known in the art, but it is preferred to use as the hydrophobicity modifier an organic silicon compound reactive with or capable of being physically adsorbed onto fumed fine silica particles or an silicone oil capable of wetting and covering the fumed silica particles.

Example of the organic silicone compounds include: hexamethyldisilazane, trimethylsilane, trimethylchlorosilane, trimethylethoxysilane, dimethyldichlorosilane, methyltrichlorosilane, allyldimethylchlorosilane, allylphenyldichlorosilane, benzyldimethylchlorosilane, bromomethyldimethylchlorosilane, $\alpha$-chloroethyltrichlorosilane, $\beta$-chloroethyltrichlorosilane, chloromethyldimethylchlorosilane, triorganosilylmercaptan, trimethylsilylmercaptan, triorganosilyl acrylate, vinyldimethylacetoxysilane, and further dimethylethoxysilane, dimethyldimethoxysilane, diphenyldiethoxysilane, hexamethyldisiloxane, 1,3-divinyltetramethyldisiloxane, 1,3-diphenyltetramethyldisiloxane, and dimethylpolysiloxanes having 2 to 12 siloxane units per molecule and containing each one hydroxyl group bonded to Si at the terminal units and the like. These may be used alone or as a mixture of two or more compounds.

The silicone oil is represented by the formula:

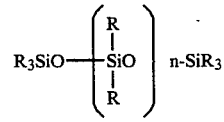

As preferable silicone oils, those having viscosities of about 5 to 5000 centistokes at 25° C. may be used, including as preferable examples methyl silicone oil, dimethyl silicone oil, phenyl methyl silicone oil, chlorophenyl methyl silicone oil, alkyl-modified silicone oil, fatty acid-modified silicone oil, polyoxyalkylene-modified silicone oil and the like. These may be employed singly or in combination.

The hydrophobicity modification may be carried out by treating the fumed silica particles with a hydrophobicity modifier after treatment of the fumed silica particles with a coupling agent as described above or by treating the fumed silica particles with a mixture of a coupling agent and a hydrophobicity modifier.

To describe about the treatment method, for example, the above treating agent for hydrophobicity modification (in some cases, a mixture of this agent with a coupling agent), optionally diluted with a suitable solvent, may be directly mixed with silica particles by a mixer such as Henschel mixer, or sprayed onto silica particles. If desired, drying is performed after the treatment to remove the solvent.

The preferable weight ratio of the coupling agent (particularly of the silane type) to the hydrophobicity modifier is within the range of 15:85 to 85:15, and the value of the triboelectric charge of the resultant developer containing the charge controller can be controlled to a desired value by varying the ratio within said range. Suitable mixing ratio also depends on the kinds of the coupling agent and the hydrophobicity modifier employed. The total quantity of the coupling agent and the hydrophobicity modifier may be preferably 0.1 to 30%, more preferably 0.5 to 20%, of the fumed silica particles.

The binder resin for the toner of the present invention may be composed of homopolymers of styrene and derivatives thereof such as polystyrene, poly-p-chlorostyrene, polyvinyltoluene, and the like; styrene copolymers such as styrene-propylene copolymer, styrene-vinyltoluene copolymer, styrene-vinylnaphthalene copolymer, styrene-methyl acrylate copolymer, styrene-ethyl acrylate copolymer, styrene-butyl acrylate copolymer, styrene-octyl acrylate copolymer, styrene-methyl methacrylate copolymer, styrene-ethyl methacrylate copolymer, styrene-butyl methacrylate copolymer, styrene-α-chloromethyl methacrylate copolymer, styrene-acrylonitrile copolymer, styrene-vinyl methyl ether copolymer, styrene-vinyl ethyl ether copolymer, styrene-vinyl ethyl ketone copolymer, styrene-butadiene copolymer, styrene-isoprene copolymer, styrene-acrylonitrile-indene copolymer, styrene-maleic acid copolymer, styrene-maleic acid ester copolymer, and the like; polymethyl methacrylate, polybutyl methacrylate, polyvinyl chloride, polyvinyl acetate, polyethylene, polypropylene, polyesters, polyurethanes, polyamides, epoxy resins, polyvinyl butyral, polyacrylic acid resin, rosin, modified rosins, terpene resin, phenol resins, aliphatic or alicyclic hydrocarbon resins, aromatic petroleum resin, chlorinated paraffin, paraffin wax, etc. These binder resins may be used either singly or as a mixture.

As the colorant to be used in the toner of the present invention, pigments or dyes known in the art such as carbon black, iron black, etc. may be employed. When the magnetic materials as described hereinafter have sufficiently dense color, these materials can substitute for at least a part of the colorant. It is also possible and preferable for imparting a stable positive charge controlling effect to use a dye known as a positive charge controller in the art in combination with the charge controller as described above of the present invention. For example, various dyes such as benzyldimethyl-hexadecylammonium chloride, decyl-trimethylammonium chloride, nigrosine base, nigrosine hydrochloride, safranine γ and crystal violet, may be used.

The developer (toner) of the present invention can be obtained by formulating the positive charge controller as prepared above into a toner comprising binder particles having at least a colorant dispersed therein. The amount of the positive charge controller may be 0.01 to 20% based on the total weight of the developer for exhibiting its effect, particularly preferably 0.1 to 3% to exhibit a positive charging characteristic with excellent stability. The charge controller may exhibit a considerable extent of effect when contained in the toner particles, but it is further preferred that 0.01 to 3% based on the developer weight of the treated charge controller particles adhere onto the toner particle surfaces. For example, while the charge controller in a quantity of several to 20% is required to accomplish the desired effect if it is contained in the toner particles, the quantity of 0.01 to 3% is sufficient when it adhere onto the toner particle surfaces. In this sense, it is preferred that the charge controller particles have a mean particle size of 0.001 to 2μ, particularly 0.002 to 0.2μ, similarly as the starting fumed silica particles, while the mean particle size of the toner may preferably be 1 to 100μ, particularly 1 to 50μ. Such an adhering state of the charge controller can be obtained by adding the charge controller particles to a toner comprising particles of a binder resin and at least a colorant dispersed therein and mixing them in a dry powder mixer utilizing a shearing force such as a Henschel mixer. The charge controller may be caused to adhere onto the toner particles which already contain another part of the charge controller inside.

In order to use the toner of the present invention in the form of a magnetic toner, magnetic powder may also be incorporated therein.

The magnetic powder to be incorporated in the toner may be of strongly magnetic elements and alloys or compounds containing them, including those known as magnetic materials such as alloys or compounds of iron, cobalt, nickel, manganese, etc. as exemplified by magnetite, hematite, ferrite, and other strongly magnetic alloys. The magnetic powder conventionally used may have a mean particle size of from 0.05 to 5μ, preferably 0.1 to 1μ. The magnetic powder may preferably be contained in an amount of 10 to 70%, more preferably 15 to 35%, based on the toner including the magnetic powder.

Further, the toner of the present invention can be mixed with carrier particles, if desired, such as iron powder, glass beads, nickel powder, ferrite powder, etc. to be used as a developer for electrostatic latent images.

The developer of the present invention is applicable to various developing methods adopted in processes generally called comprehensively as electrostatographic processes. For example, it is applicable to the magnetic brush developing method, the cascade developing method, the method as disclosed in U.S. Pat. No. 3,909,258 in which conductive magnetic toner is used, the method as disclosed in Japanese Laid-open Patent Application No. 31136/1978 in which high resistivity magnetic toner is used, the methods as disclosed in Japanese Laid-open Patent Applications Nos. 42121/1979, 18656/1980 and 43027/1979, the fur brush developing method, the powder cloud method, the impression developing method, and others.

However, one of the most attractive methods for utilizing the developer according to the present invention is that in which it is used in the form of an insulating, i.e., electro-nonconductive, magnetic developer (jumping developer) in a developing method, which comprises providing an electrostatic image bearing member for bearing electrostatic images on its surface and a developer carrying member such as a rotating sleeve arranged with a predetermined interval therebetween at the developing station, having an insulating magnetic developer carried in a thickness thinner than said interval on the developer carrying member, and transferring said developer to the aforesaid electrostatic image holding member at the developing station thereby to effect development, as disclosed in Japanese Laid-open Patent Application No. 43027/1979 or No. 18656/1980. The reasons are as follows. Thus, the above developing method belonging to the one-component developing methods is free from a drawback inherent to the two-component method employing carrier particles and toner particles that the image quality or the density may vary due to the charge in quantity proportions between these two kinds of particles and also has an excellent feature that toner image formation stable and faithful to the electrostatic image can be obtained, due to formation of a uniform and thin toner layer facing the electrostatic image bearing member, which enables uniform migration of the toner toward the electrostatic image. According to my observation, however, when copying is repeated by use of a jumping developer known in the art, evenness of the developer layer carried on the developer bearing member may sometimes be impaired, for example by formation of toner layer in streaks along the circumferential direction of the carrying member, local extreme increase in thickness of the developer layer carried as compared with the initial thickness, which may result in generation of spot-like irregularities or formation of ripples. The first irregularity may be observed as white streaks on the image when developed, while the second may be observed as density irregularities in the form of spots and the third as ripples. Such irregularities may not occur in repeated copying under usual condition, but may sometimes occur unfavorably in repeated uses in a long term particularly under the environmental conditions of extremely low temperature and low humidity.

Also, under higher temperature and higher humidity conditions, the thickness of the developer layer may sometimes unfavorably change, and become thinner in most cases, thus frequently causing lowering of image density.

As the result of investigations about this point, it has been found that one reason resides in lack of stability and reliability of the charge controller component, and that characteristics of adhesion of the developing powder onto the sleeve and transfer of the developing powder from the sleeve may vary due to change in triboelectric charge.

Explaining in further detail, such irregularities are caused by generation of ununiform portion in amount of triboelectric charges in the developer layer carried on the carrying member due to the change in the environmental conditions. More particularly, under the environmental conditions of extremely low temperature and humidity, a component of the developer with extremely large triboelectric charges is formed through friction of the carrying member surface and the developer. Due to the image force caused by the charges, such a component with extremely large triboelectric charges is liable to be accumulated in the vicinity of the carrying member and affect influences on evenness or readiness in developing of the upper layer portion of the developer, thereby causing such irregularities as white streaks, spotlike irregularities, and ripple patterns as mentioned above. The reduction in thickness of the developer layer at higher temperature and humidity may also be generated by uneven triboelectrification between the developer and the carrying member, namely due to instability of the amount of triboelectric charges of the developer near the surface of the carrying member. As another reason for such an instable amount of triboelectric charges, it may be caused partly because the triboelectrification effect on the developer particles given by the developer carrying member (sleeve roller), is somewhat weaker than that by the carrier particles in the two-component system developing method.

However, as described previously, the developer of the present invention has stably a uniform and sharp distribution of the triboelectric charges even under the conditions of higher temperature and humidity or lower temperature and humidity, and therefore it can be a developer most suited for use in the above developing method.

Next, the developing step according to the process of this invention with the use of the above developer is described.

Figure 1:
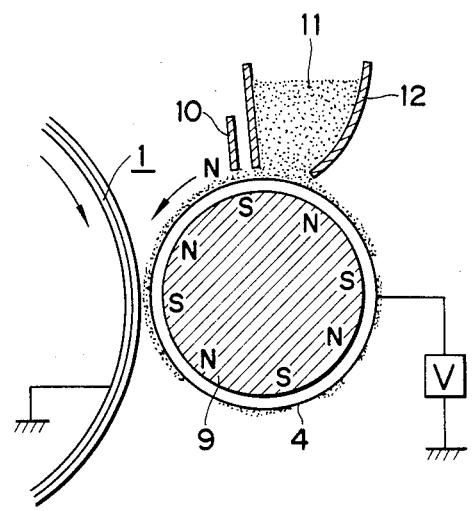
FIG. 1 shows a sectional view showing an embodiment of the developing step according to the method of this invention.

FIG. 1 shows a sectional view of one embodiment of the developing system used in the present invention. In the Figure, an electrostatic image bearing member 1 moves in the direction shown by the arrow. A non-magnetic cylinder or sleeve 4 which is a developer carrying member rotates so as to be progressed in the same direction as the movement of the surface of the electrostatic image bearing member at the developing section. Inside the non-magnetic cylinder 4 is provided a multi-polar permanent magnet 9 so as not to be rotated. One-component insulating developer 11 delivered from a developer vessel 12 is coated on the surface of the non-magnetic cylinder 4, and positive charges of opposite polarity to those of the electrostatic image are given to the toner particles. Further, a doctor blade 10 is brought to near the surface of the cylinder (interval $50\mu$ to $500\mu$) and arranged to confront one magnetic pole (S-pole in the drawing) of the multi-polar permanent magnet 9, whereby the toner layer thickness is evenly regulated thin ($30\mu$ to $300\mu$). By controlling the rotational speed of the cylinder 4, the surface layer speed and preferably the internal speed of the developer layer are made substantially equal to or approximate to the surface speed of the electrostatic image bearing member 1. As the doctor blade 10, a permanent magnet may be employed in place of an iron to form a counter-pole. Also, an alternating bias voltage may be applied between the developer carrying member and the electrostatic image bearing surface at the developing section. This alternating bias voltage may have a frequency of 200 to 4000 Hz and Vpp (peak to peak voltage) of 500 to 3000 V.

As described above, in this developing step, for the purpose of having a magnetic developer held stably on a developer carrying member, a non-magnetic cylinder 4 including a multi-polar permanent magnet 9 has been employed. Also, for the purpose of forming the developer layer thin and evenly, a doctor blade 10 made of a magnetic thin plate or a permanent magnet has been arranged in the vicinity of the surface of the cylinder 4. When such a doctor blade of a magnetic material is employed, there is formed a counter-pole against the magnetic pole of the permanent magnet included within the developer carrying member, whereby the toner particle chains are erected forcibly to advantageously regulate the developer layer thin at other portions of the developer carrying member, for example, at the developing position confronting the electrostatic image surface. Further, by giving such a forced movement to the developer, the developer layer can be made more uniform, whereby formation of thin and uniform toner layer not realized by a non-magnetic doctor blade can be accomplished. Besides, since the gap between the doctor blade and the sleeve can be set relatively wider, an effect of preventing destruction or agglomeration of the toner particles is attained. At the developing station, the toner particles may be transferred through attracting action of the electrostatic image or the action of the alternating bias voltage toward the electrostatic image side.

As described above, according to the present invention, there is provided a developer having excellent characteristics as summarized below.

First, due to the use of fine silica particles treated with a coupling agent as the charge controller and controlled to a hydrophobicity within the range from 30 to 80, particularly when employed as a developer for electrophotography, the amount of triboelectric charges between the toner particles, or the toner and the carrier, or between the toner in case of one-component system developer and a toner carrying member such as a sleeve and the distribution of triboelectric charges are made sharp and even, and thus it is made possible to control the amount of charging to the level suitable for the developing system employed, whereby fogging, and scattering of the toner around edges of the latent image which could not be sufficiently overcome in the prior art can be obviated to give a high image density and good reproducibility of half tone.

Further, when the developer is subjected to continuous use over a long term, the characteristics at the initial stage can be maintained and images of high quality can be attained for a long term.

Further, there are important specific features in practical application. One of them is that the distribution of triboelectric charges on the developer under the environmental conditions of higher temperature and humidity is sharp and not substantially changed from that under normal temperature and humidity, and therefore development can be carried out faithfully to the latent image without fog and lowering in image density, and further with excellent transfer efficiency.

Also, even when used under lower temperature and humidity conditions, the distribution of triboelectric charges is not substantially changed, without formation of a developer component with extremely great quantity of charge, and therefore, to be surprising enough, there is neither lowering in image density nor occurrence of fog, substantially without coarsening or scattering of the toner during transfer.

Another specific feature resides in the storage stability that the characteristics at the initial stage can be maintained even after storage for a long term.

Still another specific feature resides in a wide variety of applicable toner compositions because the treated silica of the present invention can be combined with any toner-constituting resins, as contrasted to the pigment or dye of the prior art, which cannot be combined with arbitrary resins but can be combined with only selected binder resins depending on the pigment or dye employed on account of its poor dispersibility. For example, the developer of the invention can be formed into not only a toner of the heat fixation type but also a pressure fixable toner or capsule toner.

Particularly, when the treated fine silica particles are attached on the toner particle surfaces, space charge controlling on the toner surfaces is primarily effected by the fine silica particles, and therefore the above mentioned effects become further marked.

Also, according to the developing method of the present invention by use of the above developer, the triboelectric charges imparted to the developer layer carried on the developer carrying member can be uniformized, permitting excessive charges, which are liable to be generated in successive copying operations under extremely lower temperature and humidity conditions, to be leaked through fine silica particles to an appropriate saturated value, and thus giving a stable developer layer. Under higher temperature and humidity conditions, the amount of triboelectric charges necessary for giving stable coating conditions can easily be maintained, thus preventing lowering of image density.

Still another specific feature resides in easy formation of a stable developer layer, whereby high image density can be obtained with good reproducibility of half tone, without causing development fog or scattering of the toner around edges of the latent image which has not been overcome in the prior art.

Having described about the basic constitution and specific features of the present invention, the present invention is now specifically described by referring to the following Examples. However, the scope of the present invention are not limited at all by these Examples.

In the following Examples, "parts by weight" and "% by weight" are written merely as "parts" and "%", respectively.

EXAMPLE 1A

| | |
|---|---|
| Styrene-butyl methacrylate copolymer | 100 parts |
| Carbon black | 2 parts |
| Nigrosine | 3 parts |

The above materials were sufficiently blended in a blender and then kneaded on a twin roll heated to 150° C. The kneaded product was left to cool, coarsely crushed by a cutter mill, pulverized by means of a micropulverizer with a jet air stream and further subjected to classification by use of a wind force classifier to obtain colored fine powder with particle sizes of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise γ-aminopropyl triethoxysilane diluted with alcohol to a treated quantity of 2.0% of the silane coupling agent based on the silica. The fine particles obtained were dried at 120° C. and thereafter placed into a Henschel mixer, and dimethyl dichlorosilane was added to the silica under stirring to a content of 2.0%. The mixture was subjected to a high speed stirring at room temperature for 2 hours, followed further by stirring at 80° C. for 24 hours, and then the mixer was opened to atmospheric pressure. This mixture was dried at atmospheric pressure under further stirring at a low speed at 60° C. for 5 hours. The treated fine silica particles obtained (positive charge controller) had a hydrophobicity of 50, a mean primary particle size of 12 mμ, and a mean secondary particle size of 0.2μ.

To 5 parts of a mixture of the above colored fine powder and 0.6% of the treated fine silica particles added and mixed therewith by a Henshcel mixer, 100 parts of iron powder carrier with particle sizes of 50 to 80μ were added and mixed to prepare a developer.

Then, according to the electrophotographic method of the prior art, negative electrostatic images were formed on an OPC sensitive material (resinous laminar coating layers containing a phthalocyanin pigment and a hydrazone compound, respectively) by subjecting it to corona-discharging at −6 KV and irradiation with original image light and subjected to powder development according to a conventional two-component magnetic brush method with the use of the above developer to form toner images, which were in turn transferred onto plain paper and fixed by heating. The transferred images obtained were found to be good with high resolution, having sufficiently high densities up to 1.5, without fog at all, being also free from scattering of the toner around the images. Transferred images were formed continuously by use of the above developer for examination of its performances under successive copying operations to give the result that the transferred image after copying 30,000 sheets was found to be totally comparable to the images at the initial stage.

When the environmental conditions were changed to 35° C. and 85% R.H., the image density was 1.39, which was a value substantially unchanged from that under normal temperature and normal humidity (i.e. 22° C., 60% R.H.) conditions, and clear images could be obtained without fog and scattering of the toner, indicating substantially the same performances up to 30,000 sheets of copying. Then, when transferred images were obtained at a low temperature and a low humidity of 10° C. and 10%, the image densities were found to be high up to 1.60, and the solid black portions could be developed and transferred very smoothly to give excellent images without scattering or drop-off of the toner. When successive copying was conducted under these environmental conditions, both continuously and intermittently, the density fluctuation was within ±0.2 up to 30,000 sheets of copying, thus showing that the developer was satisfactory in practical applications.

Figure 2A:
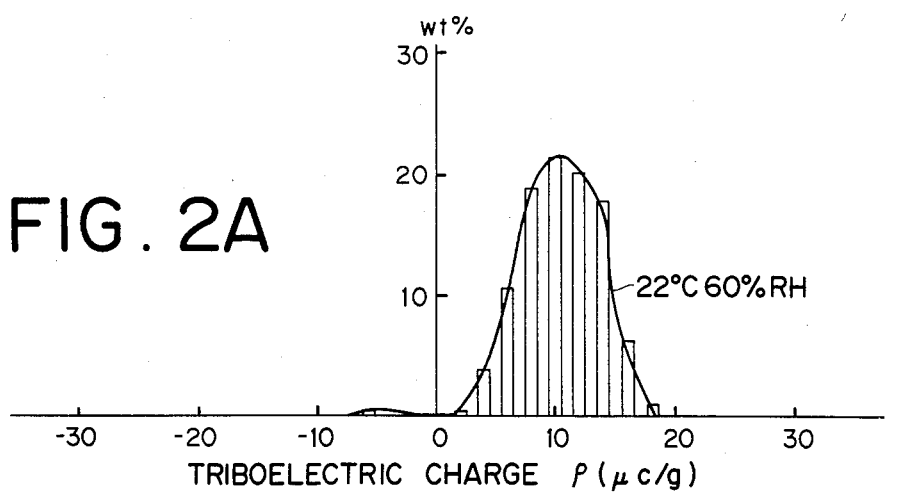
FIG. 2(a) to FIG. 2(c) and FIG. 4(a) to FIG. 4(c) are graphs showing distributions in amount of triboelectric charges under various conditions in Example 1A and 1B as described below.
Figure 2B:
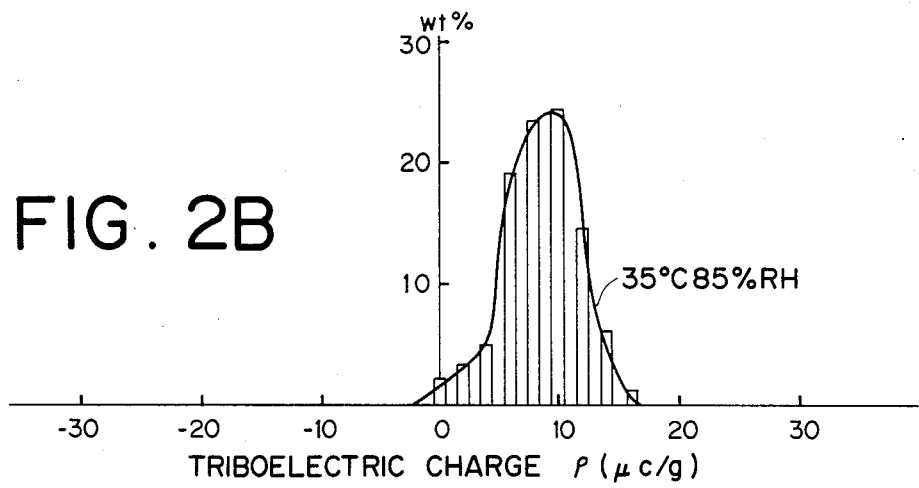
Figure 2C:
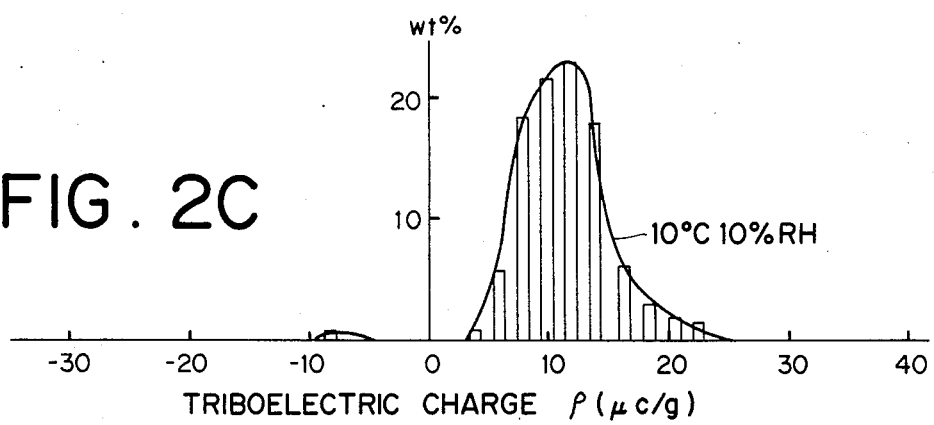

The results of measurements of the distributions in amount of triboelectric charges on this developer are shown in FIG. 2(a) through (c), which indicate sharp distributions under respective conditions of normal temperature, normal humidity; high temperature, high humidity; and low temperature, low humidity.

Comparative Example 1A

A developer was prepared in the same manner as in Example 1A, except that Aerosil 200 was not treated with γ-aminopropyltriethoxysilane nor with dimethyldichlorosilane, and development and transfer were also conducted similarly. As the result, only reversed images could be obtained, and the amount of triboelectric charges was −3.2 μc/g, exhibiting a negative charging characteristic.

COMPARATIVE EXAMPLE 2A

A developer was prepared in the same manner as in Example 1A except that no treatment with dimethyldichlorosilane was applied, and images were obtained similarly. At normal temperature and normal humidity, fog occurred little, but the image density was as low as 0.84 with conspicuous coarsening at the solid black portions. When successive copying test was conducted, the density was lowered to 0.46 on copying of 2000 sheets. When images were obtained under the conditions of 35° C. and 85%, the image density was lowered to 0.50 with increase of fog, scattering of the toner and coarsening of the image, proving to be practically unuseful. The transfer efficiency was also as low as 63%.

Figure 3A:
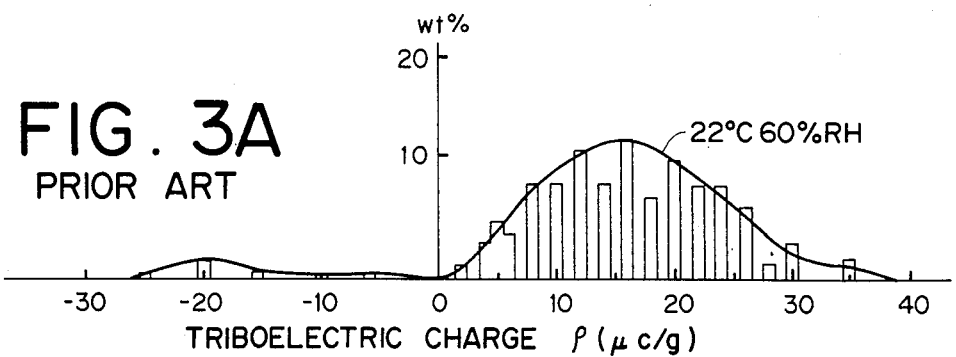
FIG. 3(a) to FIG. 3(c) are graphs showing distributions in amount of triboelectric charges under various conditions in Comparative Example 1A as described below.
Figure 3B:
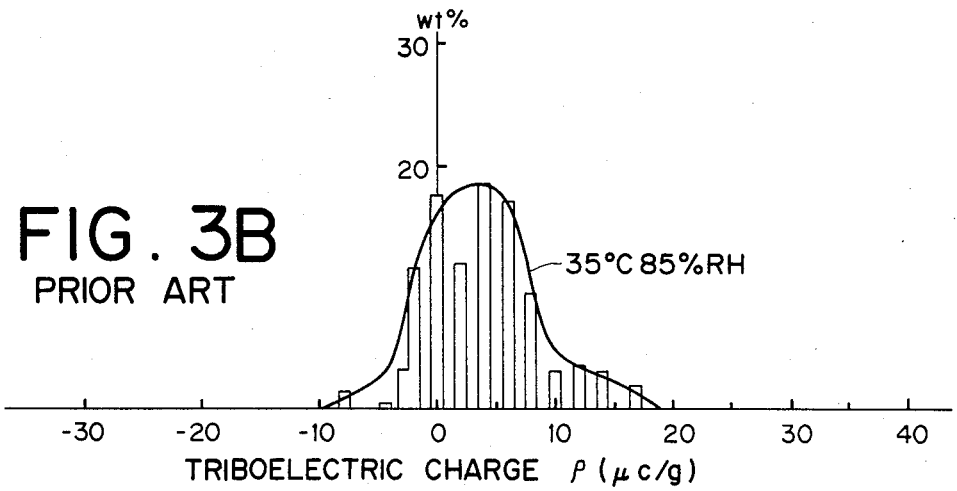
Figure 3C:
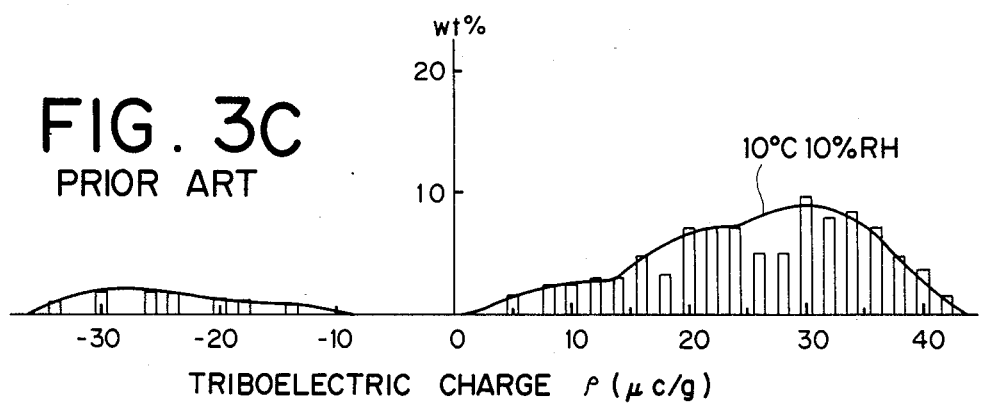

When the images were obtained under the conditions of 10° C. and 10% R.H., the image density was as low as 0.70, with excessive scattering, fog and coarsening, and transfer drop-off was markedly observed. Continuous image formation was effected until about 500 copies were produced, when the density became 0.40 to make copying no longer practically possible. The results of measurements of the triboelectric charge distributions on this developer are shown by the full lines in FIGS. 3(a) through (c). As described above, its distribution was broad in any environment, evidencing a large content of components having deleterious effects on development and transfer.

EXAMPLES 2A–5A

When Example 1A was repeated except that the amounts of γ-aminopropyl triethoxysilane and dimethyldichlorosilane treated on Aerosil 200 were changed to 0.5%, 1.0%; 2.0%, 5.0%; 10.0%, 5.0%; and 10.0%, 10.0%, respectively, good results could be obtained.

EXAMPLE 6A

| Styrene-butyl methacrylate copolymer | 100 parts |
| Carbon black | 2 parts |
| Nigrosine | 3 parts |
| Fine silica powders prepared in Example 1 | 10 parts |

The above components were kneaded, pulverized and classified to obtain fine powder with particle sizes of 5 to 20μ, and further the silica particles prepared in Example 1A were added to and mixed with the above fine powder in an amount of 0.3% based on said fine powder. Otherwise, the procedure of Example 1A was substantially followed to obtain good results.

EXAMPLE 7A

Substantially the same procedure as in Example 1A was repeated except that N,N-dimethylaminophenyl triethoxysilane was employed in place of γ-aminopropyl triethoxysilane, whereby good results were obtained.

EXAMPLE 8A

Substantially the same procedure as in Example 1A was repeated except that aminoethylaminomethylphenethyl triethoxysilane was employed in place of γ-aminopropyl triethoxysilane, whereby good results were obtained.

EXAMPLE 9A

| Polyethylene | 100 parts |
| Carbon black | 1 part |
| Spirit black | 2 parts |

Except for preparing a toner from the above materials according to the method as described in Example 1A, the same procedure as in Example 1A was followed to give good results.

Evaluations of respective Examples and Comparative Examples mentioned above are shown in Table 1.

TABLE 1

| | Normal Temperature, Normal Humidity | | | | | | | 35° C. 85% | |
|---|---|---|---|---|---|---|---|---|---|
| | Image density | Fog | Scattering | Resolution | Density on copying 30000 sheets | Average amount of triboelectric charges μc/g | Standard deviation | Image density | Transfer efficiency (%) |
| Example | | | | | | | | | |
| 1A | 1.50 | good | good | good | 1.39 | +11.0 | 2.9 | 1.39 | 89 |
| 2A | 1.32 | good | good | good | 1.30 | +5.2 | 3.4 | 1.27 | 87 |
| 3A | 1.46 | good | good | good | 1.40 | +7.4 | 3.1 | 1.31 | 87 |
| 4A | 1.35 | good | good | good | 1.30 | +10.5 | 2.7 | 1.20 | 87 |
| 5A | 1.41 | good | good | good | 1.31 | +8.7 | 3.0 | 1.20 | 89 |
| 6A | 1.29 | good | good | good | 1.25 | +7.2 | 2.4 | 1.20 | 90 |
| 7A | 1.41 | good | good | good | 1.35 | +7.6 | 2.5 | 1.35 | 93 |
| 8A | 1.36 | good | good | good | 1.30 | +9.1 | 3.0 | 1.28 | 90 |
| Comparative Example | | | | | | | | | |
| 1A | 0.07 | reversed | bad | bad | — | −3.2 | 7.0 | No image obtained | — |
| 2A | 0.84 | bad | bad | bad | on copying 2000 sheets 0.46 | +15.0 | 11.0 | 0.50 | 63 |

| | 35° C. 85% | | | 10° C. 10% | | | | | |
|---|---|---|---|---|---|---|---|---|---|
| | Density on copying 30000 sheets | Average amount of triboelectric charges μc/g | Standard deviation | Image density | Transfer efficiency (%) | Density on copying 30000 sheets | Average amount of triboelectric charges μc/g | Standard deviation | Hydrophobicity of silica |
| Example | | | | | | | | | |
| 1A | 1.30 | +8.0 | 3.4 | 1.60 | 92 | 1.40 | +12.0 | 3.2 | 50 |
| 2A | 1.30 | +4.8 | 3.6 | 1.20 | 90 | 1.35 | +5.9 | 3.5 | 35 |
| 3A | 1.35 | +6.1 | 3.1 | 1.39 | 87 | 1.36 | +7.6 | 3.5 | 60 |
| 4A | 1.25 | +8.4 | 3.7 | 1.20 | 86 | 1.31 | +11.2 | 3.2 | 60 |
| 5A | 1.28 | +6.7 | 3.4 | 1.45 | 88 | 1.40 | +9.0 | 3.2 | 80 |
| 6A | 1.29 | +6.2 | 3.4 | 1.35 | 91 | 1.40 | +7.5 | 3.0 | 50 |
| 7A | 1.35 | +6.8 | 3.0 | 1.32 | 90 | 1.35 | +8.0 | 3.0 | 70 |
| 8A | 1.26 | +8.5 | 3.2 | 1.32 | 90 | 1.35 | +9.5 | 3.4 | 70 |
| Comparative Example | | | | | | | | | |
| 1A | — | −0.5 | 5.5 | 0.05 | 35 | 0.12 | −11.0 | 10.3 | 0 |
| 2A | 0.20 | +2.7 | 8.5 | 0.70 | 70 | On copying 500 sheets 0.40 | +26.0 | 21.0 | 0 |

EXAMPLE 1B

In Example 1A, fine silica particles Aerosil 200 were subjected to the heat treatment at 800° C. for one hour and otherwise the same procedure as in Example 1A was followed to obtain treated fine silica particles with a hydrophobicity of 55.

With the use of the treated fine silica particles similarly as in Example 1A, a developer was prepared, and development of negative electrostatic images according to the magnetic brush method and transfer onto plain paper were performed. The image densities obtained under various conditions are shown below. The developer characteristics including the results of successive copying tests were equal to or better than those obtained in Example 1A.

| | |
|---|---|
| 22° C., 60% R.H. | 1.53 |
| 35° C., 85% R.H. | 1.50 |
| 10° C., 10% R.H. | 1.50 |

Also, as the test for examination of storage stability, the developer was stored under the conditions of 35° C., 90% R.H. for one month, and even after the storage test, the image obtained was clear substantially without lowering of image density as compared with that before storage.

The results of measurement of the distributions of triboelectric charges on this developer are shown in FIGS. 4(a) through (c), which exhibit further sharper distributions than those in Example 1A under the respective conditions of normal temperature and normal humidity, higher temperature and higher humidity, and lower temperature and lower humidity.

COMPARATIVE EXAMPLE 1B

A developer was prepared in the same manner as in Example 1B, except that Aerosil 200 was not treated with γ-aminopropyltriethoxysilane and dimethyldichlorosilane, and development and transfer were also conducted similarly. The results obtained were unsatisfactory, similarly as in Comparative Example 1A.

COMPARATIVE EXAMPLE 2B

A developer was prepared in the same manner as in Example 1B except that no treatment with dimethyldichlorosilane was applied, and images were obtained similarly. The results obtained were unsatisfactory, similarly as in Comparative Example 2A.

EXAMPLES 2B-9B

When Example 1B was repeated except that the heat treatment temperatures were changed to 430° C., 480° C., 500° C., 600° C., 700° C., 900° C., 1000° C., 1200° C., respectively, good results could be obtained.

EXAMPLE 10B

When Example 1B was repeated except that the amounts of γ-aminopropyltriethoxysilane and dimethyldichlorosilane treated on Aerosil 200 were changed to 10% and 5.0%, respectively, good results could be obtained.

EXAMPLE 11B

| | | |
|---|---|---|
| Polyethylene | 100 | parts |
| Carbon black | 1 | part |
| Spirit black | 2 | parts |

The above materials were made into a toner according to the same procedure as in Example 1B, following otherwise the same procedure as in Example 1B. As the result, good results could be obtained.

The results of evaluation of Examples 1B to 11B are summarized in Table 2 together with those of Comparative Examples 1B and 2B.

TABLE 2

| | Before storage | | | After stored at 35° C., 90% R.H., for one month | | | |
|---|---|---|---|---|---|---|---|
| | Image density | Amount of triboelectric charges μc/g | Standard deviation | Image density | Amount of triboelectric charges μc/g | Standard deviation | Hydrophobicity of silica |
| Example | | | | | | | |
| 1B | 1.53 | +11.5 | 2.5 | 1.50 | +10.5 | 2.9 | 55 |
| 2B | 1.40 | +8.5 | 3.4 | 1.35 | +8.3 | 3.5 | 50 |
| 3B | 1.42 | +9.1 | 3.4 | 1.38 | +9.0 | 3.5 | 50 |
| 4B | 1.38 | +9.0 | 3.3 | 1.36 | +8.5 | 3.9 | 55 |
| 5B | 1.50 | +9.5 | 3.0 | 1.45 | +9.3 | 3.5 | 58 |
| 6B | 1.47 | +9.6 | 2.9 | 1.47 | +9.5 | 3.3 | 55 |
| 7B | 1.47 | +9.6 | 3.4 | 1.47 | +9.2 | 3.2 | 55 |
| 8B | 1.40 | +9.9 | 3.1 | 1.35 | +9.7 | 3.0 | 60 |
| 9B | 1.42 | +8.2 | 3.2 | 1.42 | +8.0 | 3.8 | 60 |
| 10B | 1.52 | +7.5 | 2.5 | 1.50 | +7.5 | 2.8 | 75 |
| 11B | 1.27 | +9.2 | 2.8 | 1.19 | +9.0 | 3.6 | 55 |
| Comparative Example | | | | | | | |
| 1B | 0.07 | −3.2 | 7.0 | No image obtained | −1.0 | 6.5 | 0 |
| 2B | 0.84 | +15.0 | 11.0 | 0.60 | +3.3 | 7.2 | 0 |

EXAMPLE 1C

| | |
|---|---|
| 3-Chloropropyl trimethoxysilane | 50 g |
| Methyl iodine | 0.5 g |
| 2-(Dimethylamino)ethyl methacrylate | 50 g |
| Dimethylformamide | 100 g |

The above mixture was allowed to react under reflux at 90° C. for 50 hours to obtain a product:

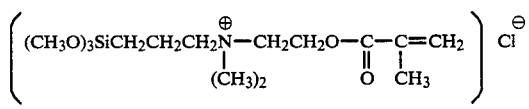

Next, 100 g of fine silica particles Aerosil 200 (produced by Nippon Aerosil Co.) were immersed in an aqueous solution having diluted 2 g of the above product, and the mixture was stirred at 60° C. for one hour. Then, the mixture was filtered and dried at 100° C. for 10 hours to obtain fine silica particles treated with a cation type unsaturated amine. The silica was placed into a Henschel mixer, and dimethyldichlorosilane was sprayed onto the silica under stirring to a quantity of 5%. High speed stirring was continued at room temperature for 2 hours, and the mixture was further stirred at 80° C. for 24 hours, followed by opening of the mixer to atmospheric pressure. The mixture was further subjected to drying at low speed under atmospheric pressure at 60° C. for 5 hours. The thus prepared treated silica had a hydrophobicity of 60.

| | |
|---|---|
| Styrene-butadiene copolymer (70:30) | 100 parts |
| Carbon black | 2 parts |
| Nigrosine | 3 parts |

As the next step, the above materials were sufficiently blended in a blender and then kneaded on a twin roll heated to 150° C. The kneaded product was left to cool, coarsely crushed by a cutter mill, pulverized by means of a micropulverizer with a jet air stream and further subjected to classification by use of a wind force classifier to obtain colored fine powder of 5 to 20μ.

A developer was prepared by adding 100 parts of iron powder carrier with particle sizes of 50 to 80μ to 5 parts of a mixture prepared by adding 0.6% of the above treated silica to the colored fine powder.

With the use of this developer, following otherwise the same procedure as in Example 1A, development of the negative electrostatic images according to the magnetic brush method and transfer onto plain paper were performed. The image densities obtained under various conditions are shown below. The developer characteristics including the results of successive copying tests were found to be substantially as good as those obtained in Example 1A.

| | |
|---|---|
| 22° C., 60% R.H. | 1.31 |
| 35° C., 85% R.H. | 1.25 |
| 10° C., 10% R.H. | 1.35 |

COMPARATIVE EXAMPLE 1C

A developer was prepared in the same manner as in Example 1C, except that Aerosil 200 was not treated with the compound prepared in Example 1C and dimethyldichlorosilane, and development and transfer were also conducted similarly. As the result, only reversed images could be obtained, and the amount of triboelectric charges was −2.8 μc/g, exhibiting a negative charging characteristic.

COMPARATIVE EXAMPLE 2C

A developer was prepared in the same manner as in Example 1C except that no treatment with dimethyldichlorosilane was applied, and images were obtained similarly. At normal temperature and normal humidity, fog and scattering occurred frequently, and the image density was as low as 0.65. Also, the image exhibited coarsening tendency, proving to be practically unuseful.

EXAMPLES 2C–4C

When Example 1C was repeated under substantially the same conditions except that the amounts of the compound prepared in Example 1C and dimethyldichlorosilane treated on Aerosil 200 were changed to 0.3%, 1.0%; 1.0%, 1.0%; and 5.0%, 1.0%, respectively, good results could be obtained.

EXAMPLE 5C

CH$_2$=C(CH$_3$)COOCH$_2$CH$_2$—N(CH$_3$)$_2$    4 g

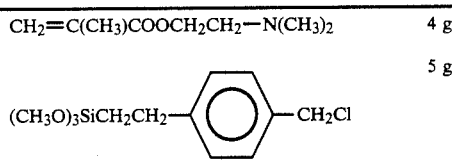   5 g

| Methyliodide | 0.5 g |
| t-Butyl alcohol | 50 g |
| Sulfur | 0.3 g |

The above mixture was refluxed as 100° C. for one hour to obtain a product:

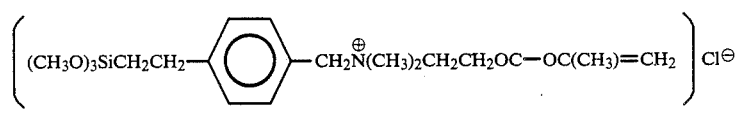

Subsequently, fine silica particles of Aerosil 200 were mixed in a Henschel mixer with the above product by spraying an aqueous solution thereof to a content of 5%. Then, the mixture was dried at 100° C. for 10 hours to obtain fine silica particles treated with a cation type unsaturated amine. The silica was again thrown into a Henschel mixer, and dimethyldichlorosilane was sprayed onto said silica under stirring to a quantity of 2%. Then, the same treatments as in Example 1C were applied. The hydrophobicity was found to be 50.

| Polyethylene oxide | 100 parts |
| Carbon black | 3 parts |
| Nigrosine | 3 parts |

With the use of the above materials, the same procedure as described in Example 1C was repeated to obtain fine powder of 5 to 25μ. A developer was prepared by adding 100 parts of iron powder carrier of particle sizes of 100 to 200μ to 10 parts of a mixture prepared by adding 0.3% of the above treated silica to the fine powder.

Next, images were obtained similarly as in Example 1C, followed by pressure fixing. The image density was found to be sufficiently high up to 1.53, and also faithful to the latent image. As the result of successive copying tests, the images obtained were practically satisfactory until copying of 20,000 sheets, and excellent characteristics were exhibited under higher temperature and higher humidity conditions of 35° C. and 85% R.H., as well as under lower temperature and lower humidity conditions of 10° C. and 10% R.H.

Evaluations of Examples 1C–5C and Comparative Examples 1C and 2C are listed in Table 3.

TABLE 3

| | Normal Temperature, Normal Humidity | | | | 35° C. 85% | | | 10° C. 10% | | | Hydrophobicity of silica |
|---|---|---|---|---|---|---|---|---|---|---|---|
| | Image density | Density on copying 30000 sheets | Fog | Scattering | Resolution | Image density | Density on copying 30000 sheets | Transfer efficiency (%) | Image density | Image density on copying 30000 sheets | Transfer efficiency (%) | |
| Example | | | | | | | | | | | | |
| 1C | 1.31 | 1.20 | Good | Good | Good | 1.25 | 1.16 | 83 | 1.35 | 1.28 | 90 | 60 |
| 2C | 1.22 | 1.18 | Good | Good | Good | 1.15 | 1.24 | 85 | 1.25 | 1.25 | 88 | 62 |
| 3C | 1.26 | 1.28 | Good | Good | Good | 1.18 | 1.16 | 88 | 1.30 | 1.34 | 90 | 60 |
| 4C | 1.35 | 1.28 | Good | Good | Good | 1.21 | 1.12 | 85 | 1.27 | 1.17 | 90 | 60 |
| 5C | 1.53 | On copying 20000 sheets 1.20 | Good | Good | Good | 1.30 | On copying 20000 sheets 1.10 | 88 | 1.32 | On copying 20000 sheets 1.10 | 92 | 50 |
| Comparative Example | | | | | | | | | | | | |
| 1C | Reversed | — | Reversed | Bad | Bad | No image | — | — | Reversed | — | — | 0 |
| 2C | 0.65 | On copying 1000 sheets 0.30 | Bad | Bad | Bad | 0.42 | — | 60 | 0.31 | — | 60 | 0 |

EXAMPLE 1D

| Styrene-butyl methacrylate copolymer | 100 parts |
| Carbon black | 2 parts |
| Nigrosine | 3 parts |

The above materials were well blended in a blender and then kneaded on a twin roll heated to 150° C. The kneaded product was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise γ-aminopropyl triethoxysilane diluted with alcohol to a treated quantity of 5.0% of the silane coupling agent based on silica. The fine particles obtained were dried at 120° C. and thereafter placed again into a Henschel mixer, and dimethyl silicone oil (viscosity: 100 centipoise at 25° C.) was added to the silica under stirring to a quantity of 2.0%. The mixture was subjected to a high speed stirring at room temperature for 2 hours, followed further by stirring continued at 160° C. for 15 hours, and then the mixer was opened to atmospheric pressure. This mixture was further dried at room temperature under atmospheric pressure for 5 hours. The degree of hydrophobicity was found to be 70.

To 10 parts of a mixture of 0.4% of the treated fine silica particles added to and mixed with the aforesaid fine powder by a Henschel mixer, 100 parts of iron powder carrier with particle sizes of 100 to 130μ were added to prepare a developer.

With the use of this developer, following otherwise the same procedure as in Example 1A, development of the negative electrostatic images according to the magnetic brush method and transfer onto plain paper were performed. The image densities obtained under various conditions are shown below. The developer characteristics were substantially comparable to those obtained in Example 1A.

| 22° C., 60% R.H. | 1.4 |
| 35° C., 85% R.H. | 1.30 |
| 10° C., 10% R.H. | 1.45 |

In successive copying tests, no abnormality was observed until 100,000 sheets of copying, and the density fluctuation was practically satisfactory within ±0.3.

COMPARATIVE EXAMPLE 1D

A developer was prepared in the same manner as in Example 1D, except that Aerosil 200 was not treated with γ-aminopropyltriethoxysilane and dimethyl silicone oil, and development and transfer were also conducted similarly. As the result, only reversed images could be obtained, and the amount of triboelectric charges was −3.2 μc/g, exhibiting a negative charging characteristic. The hydrophobicity of silica was found to be 0.

COMPARATIVE EXAMPLE 2D

A developer was prepared in the same manner as in Example 1D except no treatment with dimethyl silicon oil was applied, and images were obtained similarly. At normal temperature and normal humidity, fog occurred little, but the image density was as low as 0.84 with conspicuous coarsening at the solid black portions. When successive copying test was conducted, the density was lowered to 0.46 on copying of 2000 sheets, and image flow occurred on copying 3000 sheets. When images were obtained under the conditions of 35° C. and 85%, the image density was lowered to 0.50 with increase of fog, scattering of the toner and coarsening of the image, thus being practically unuseful. The transfer efficiency was also as low as 63%. The hydrophobicity of silica was 0.

When images were obtained under the conditions of 10° C. and 10% R.H., the image density was as low as 0.70, with excessive scattering, fog and coarsening, and transfer drop-off was markedly observed. Continuous image formation was effected until about 500 copies were obtained, when the density became 0.40 to make copying no longer practically possible.

EXAMPLE 2D

Example 1D was repeated except for using methyl hydrogen silicone oil (trade name: TSF 484, produced by Toshiba Silicone Co.) in place of dimethyl silicone oil, whereby good results were obtained.

EXAMPLE 3D

| Polyethylene | 100 parts |
| Carbon black | 1 part |
| Spirit black | 2 parts |

The above materials were made into a toner according to the same procedure as in Example 1D, following otherwise the same procedure as in Example 1D. As the result, good results could be obtained.

EXAMPLE 4D

The experiment was conducted in substantially the same manner as in Example 1D except for replacing γ-aminopropyltriethoxysiline with N,N-dimethylaminophenyl triethoxysilane to obtain good results. The hydrophobicity of silane was 75. The results of evaluation of Examples 1D to 4D are summarized in Table 4 together with those of Comparative Examples 1D and 2D.

TABLE 4

| | Normal Temperature, Normal Humidity | | | | | 35° C. 85% | | | |
| | Image density | Density on copying 100000 sheets | Fog | Scattering | Resolution | Image density | Density on copying 100000 sheets | Transfer efficiency (%) | Image flow |
| --- | --- | --- | --- | --- | --- | --- | --- | --- | --- |
| Example | | | | | | | | | |
| 1D | 1.40 | 1.31 | Good | Good | Good | 1.30 | 1.26 | 92 | Good |
| 2D | 1.33 | 1.30 | Good | Good | Good | 1.18 | 1.24 | 90 | Good |
| 3D | 1.60 | 1.40 | Good | Good | Good | 1.41 | 1.36 | 90 | Good |
| 4D | 1.36 | 1.30 | Good | Good | Good | 1.25 | 1.20 | 92 | Good |
| Comparative Example | | | | | | | | | |
| 1D | Reversed | — | — | Bad | Bad | Bad | No image | — | — | — |
| 2D | 0.84 | — | Fair | Bad | Bad | 0.50 | — | 63 | Bad |

TABLE 4-continued

|  | After storage for one month at 35° C., 90% R.H. | | | | 10° C. 10% | | | generated on copying of 3000 sheets |
| --- | --- | --- | --- | --- | --- | --- | --- | --- |
|  | Image density | Fog | Scattering | Resolution | Image density | Density on copying 100000 sheets | Transfer drop-off | Scattering |
| Example | | | | | | | | |
| 1D | 1.30 | Good | Good | Good | 1.35 | 1.15 | Good | Good |
| 2D | 1.26 | Good | Good | Good | 1.35 | 1.24 | Good | Good |
| 3D | 1.42 | Good | Good | Good | 1.60 | 1.43 | Good | Good |
| 4D | 1.30 | Good | Good | Good | 1.35 | 1.28 | Good | Good |
| Comparative Example | | | | | | | | |
| 1D | Pale reversed image | Bad | Bad | Bad | Reversed | — | — | — |
| 2D | 0.58 | Bad | Bad | Bad | 0.70 | On copying 500 sheets 0.40 | Fair | Bad |

EXAMPLE 1E

| Styrene-butadiene copolymer (70:30) | 100 parts |
| --- | --- |
| Carbon black | 3 parts |
| Nigrosine | 4 parts |

The above materials were well blended in a blender and then kneaded on a twin roll heated to 150° C. The kneaded produce was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise isopropyl tri-isostearoyl titanate diluted with alcohol to a treated quantity of 2.0% of the titanium coupling agent based on the silica. The fine particles obtained were dried at 120° C.

A developer was prepared by adding 100 parts of iron powder carrier with particle sizes of 50 to 80μ to 5 parts of a mixture prepared by adding 0.6% of the treated silica to the above fine powder. The amount of triboelectric charges was as high as ±18.6 μc/g.

With the use of this developer, following otherwise the same procedure as in Example 1A, development of the negative electrostatic images according to the magnetic brush method and transfer onto plain paper were performed. The image densities obtained under various conditions are shown below. The developer characteristics were substantially comparable to those obtained in Example 1A.

| 22° C., 60% R.H. | 1.5 |
| --- | --- |
| 35° C., 85% R.H. | 1.42 |
| 10° C., 10% R.H. | 1.40 |

In successive copying tests, no abnormality was observed until 100,000 sheets of copying, and the density fluctuation was practically satisfactory within ±0.2.

After this developer was stored under an environment of 35° C. and 90% R.H. for one month, images were also obtained by use of this developer, whereby the image density was substantially unchanged as 1.38 and the image quality was also good.

COMPARATIVE EXAMPLE 1E

A developer was prepared in the same manner as in Example 1E, except that Aerosil 200 was not treated with isopropyl tri-isostearoyl titanate, and development and transfer were also conducted similarly. As the result, only reversed images could be obtained, and the amount of triboelectric charges was −3.0 μc/g, exhibiting a negative charging characteristic.

EXAMPLE 2E

Example 1E was repeated except for replacing isopropyl tri-stearoyl titanate with isopropyl tri(N, N-dimethylethylamino)titanate, whereby there were obtained images of a high density of 1.31 which are faithful to latent images having high resolution without fog, scattering or transfer drop-off.

After successive copying tests of 100,000 sheets, the images obtained were comparable to those at the initial stage. After storage under an environment of 35° C. and 90% R.H. for one month, this developer was employed for image formation to give the result that the image density was 1.30 as before, and the image quality was also good. When image formation was effected at 35° C., 85% R.H., very good images could be obtained from the initial stage, and the images after 100,000 sheets of copying were also good. The transfer efficiency was also excellent and as high as 92%.

EXAMPLE 3E

Example 1E was repeated except that dianthranylethylene titanate was used for treating in an amount of 10% on the silica in place of isopropyl tri-stearoyl titanate. The resultant developer exhibited excellent image quality and durability under respective environments of lower temperature and lower humidity, higher temperature and higher humidity, and normal temperature and normal humidity.

EXAMPLE 1F

A mixture of 100 parts of zinc oxide, 20 parts of styrene-butadiene copolymer, 40 parts of n-butyl methacrylate, 120 parts of toluene and 4 parts of 1% Rose Bengal solution in methanol was dispersed by mixing in a ball mill for 6 hours. This dispersion was applied as a coating by a wire bar on an aluminum plate of 0.05 mm thickness in an amount to give a dry coating thickness of 40μ, followed by evaporation of the solvent by hot air to prepare a zinc oxide-binder type photosensitive material, which was then formed into a shape of drum. This photosensitive material was subjected to corona discharging at −6 KV to be charged evenly over all the surface, and thereafter an original image irradiation was effected to form an electrostatic latent image.

A developer carrying member in the form of a cylindrical sleeve of stainless steel with an outer diameter of 50 mm was used. A magnetic flux density on the sleeve surface of 700 Gauss was applied, and a distance between the doctor blade and the sleeve surface was set at 0.2 mm. A rotary sleeve fixed magnet type developing device was set at a distance of 0.25 mm between the aforesaid photosensitive drum surface and the sleeve surface (the circumferential velocity of the sleeve being the same as that of the drum, with rotational directions opposite to each other), and an alternating voltage of 400 Hz, 1000 V and a direct bias voltage of −150 V were applied on the sleeve.

One hundred (100) parts of Priorite S-5A (styrene-butadiene copolymer, produced by Goodyear Chemicals), 60 parts of magnetite and 3 parts of nigrosine spirit were mixed well in a blender and then kneaded on a twin roll heated to 150° C. The kneaded product was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise γ-aminopropyl triethoxysilane diluted with alcohol to a treated quantity of 10% of the silane coupling agent based on the silica. The fine particles obtained were dried at 120° C. and thereafter placed again into a Henschel mixer, and dimethyl dichlorosilane was sprayed onto the silica under stirring to a content of 10%. The mixture was subjected to a high speed stirring at room temperature for 2 hours, followed further by stirring continued at 80° C. for 24 hours, and then the mixer was opened to atmospheric pressure. This mixture was dried at atmospheric pressure under further stirring at a low speed at 60° C. for 5 hours. The hydrophobicity of the treated silica was 60.

The thus treated fine silica particles were added in an amount of 0.6% to the above colored fine powder, followed by mixing by a Henschel mixer to provide a developer. Development was carried out with the use of this developer, and then the powder image was transferred to a paper while irradiating a direct current corona of −7 V on the back face of the paper to obtain a copied image. Fixing was effected by means of a commercially available plain paper copying machine (trade name: NP-5000, produced by Canon, Inc.).

The transferred image obtained had a sufficiently high density of 1.5, with no fog at all, and it was a good image with high resolution without any scattering of the toner around the image. The weight of the coating toner layer formed on the sleeve was $1.5 \times 10^{-3}$ (g/cm$^2$).

When successive copying test was performed by preparing continuously transferred images with the use of the above developer, the transferred images after copying 100,000 sheets were fairly comparable to those at the initial stage.

When the environmental conditions were changed to 35° C. and 85% R.H., the image density was 1.40 which was substantially to that obtained at normal temperature and normal humidity, clear images were obtained without fog or scattering of the toner, and there was substantially no change in performances until 100,000 sheets of copying during successive copying test. The weight of the toner layer per unit area was $1.3 \times 10^{-3}$ g/cm$^2$. Next, when a transferred image was obtained at lower temperature and lower humidity of 10° C. and 10% R.H., the image density was as high as 1.47, with the solid black portion being smoothly developed and transferred, thus giving an excellent image without scattering or drop-off of the toner. When successive copying tests were performed under these environmental conditions, continuously and intermittently, the density fluctuation was ±0.1 until copying of 100,000 sheets and was practically satisfactory, without appearance of white streak or irregularity. The change in weight of the toner layer per unit area during the tests is shown in FIG. 5(a), which indicates that there was substantially no change.

COMPARATIVE EXAMPLE 1F

A developer was prepared in the same manner as in Example 1F, except that Aerosil 200 was not treated with γ-aminopropyltriethoxysilane or dimethyldichlorosilane, and development and transfer were also conducted similarly. As the result, only reversed images could be obtained, and the amount of triboelectric charges was −3.2 μc/g, exhibiting a negative charging characteristic.

COMPARATIVE EXAMPLE 2F

A developer was prepared in the same manner as in Example 1F except that no treatment with dimethyldichlorosilane was applied, and images were obtained similarly. At normal temperature and normal humidity, fog occurred little, but the image density was as low as 0.76 with conspicuous coarsening at the solid black portions. When successive copying test was conducted, the density was lowered to 0.58 on copying of 5000 sheets. When images were obtained under the conditions of 35° C. and 85%, the image density was lowered to 0.63 with increase of fog, scattering of the toner and coarsening of the image, proving to be practically unuseful. The transfer efficiency was also as low as 70%. The weight of the toner layer per unit area was $0.70 \times 10^{-3}$ g/cm$^2$. When the images were obtained under the conditions of 10° C. and 10% R.H., the image density was as low as 0.70, with excessive scattering, fog and coarsening, and transfer drop-off was markedly observed. Continuous image formation was effected until after about copying of about 5000 sheets, the density became 0.40 to make copying no longer practically possible. The toner weight per unit area at the initial stage was $1.7 \times 10^{-3}$ g/cm$^2$, which became increased to $3.5 \times 10^{-3}$ g/cm$^2$, with formation of wave pattern or irregularity.

COMPARATIVE EXAMPLE 3F

Example 1F was repeated except that the amount of dimethyldichlorosilane was changed to 0.1% based on the silica. The hydrophobicity of the treated silica was found to be 15. Until copying 100,000 sheets under normal temperature and normal humidity conditions in successive copying test, good images could be obtained without change of the toner weight of the toner layer per unit area. However, at 35° C. and 85%, the image density at the initial stage was 1.2, which was lowered to 0.78 on copying of 5,000 sheets. The toner layer weight, which was $1.4 \times 10^{-3}$ g/cm$^2$ at the initial stage, was lowered to $0.75 \times 10^{-3}$ g/cm$^2$, on copying of 5,000 sheets.

After storage under the conditions of 10° C. and 10% for one month, successive copying test was conducted under the same conditions, whereby the image density at the initial stage was as good as 1.4, but ripple pattern or irregularity occurred on copying of 5,000 sheets, with lowering of the image density to 0.62, and white streaks appeared on the image on copying of 7,000 sheets. And, the weight of the toner layer was found to be increased to $3.9 \times 10^{-3}$ g/cm$^2$. The changes in the weight of the toner layer per unit area during this operation are shown in FIG. 5(b).

EXAMPLE 2F

The experiment was carried out in substantially the same manner as in Example 1F, except for using N,N-dimethylaminophenyl triethoxysilane in place of γ-aminopropyltriethoxysilane. As the result, the coating was stable to give good results. The hydrophobicity of the silica was found to be 75.

EXAMPLE 3F

The experiment was carried out in substantially the same manner as in Example 1F, except for using aminoethylaminomethylphenethyl triethoxysilane in place of γ-aminopropyl triethoxysilane. As the result, the coating was stable to give good results. The hydrophobicity of the silica was found to be 45.

EXAMPLE 1G

| | |
|---|---|
| Styrene-butyl methacrylate copolymer | 100 parts |
| Magnetite | 60 parts |
| Carbon black | 2 parts |
| Nigrosine | 3 parts |

The above materials were well blended in a blender and then kneaded on a twin roll heated to 150° C. The kneaded product was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 were subjected to the heat treatment at 800° C. for one hour, and the resultant particles were treated similarly as in Example 1F to obtain treated fine silica particles with a hydrophobicity of 55.

The thus treated silica particles were added to the above colored fine powder in an amount of 0.6%, followed by mixing in a Henschel mixer, to provide a developer.

Then, an OPC photosensitive member as used in Example 1A was applied with −6 KV corona discharging to be charged over the entire surface thereof, and irradiated with an original image to form electrostatic latent images thereon.

Development and transfer were conducted in the same manner as in Example 1F, except that this photosensitive member was combined with the developer carrying member of Example 1F and the developer as prepared above was employed. The image densities of the transferred images and the toner weights on the sleeve under various atmospheric conditions are shown below, and the developing characteristics including the results of successive copying test were satisfactory, being substantially equal to those of Example 1F.

| | Density | Toner weight |
|---|---|---|
| 22° C., 60% R.H. | 1.38 | $1.5 \times 10^{-3}$ g/cm$^2$ |
| 35° C., 85% R.H. | 1.30 | $1.40 \times 10^{-3}$ g/cm$^2$ |
| 10° C., 10% R.H. | 1.31 | — |

The changes in weight of the toner layer per unit area in successive copying test at lower temperature and lower humidity of 10° C. and 10% R.H. are shown in FIG. 6(a), which indicates that there was no substantial change. Also, when developed after storage at 35° C., 90% R.H. the results obtained were substantially the same as before storage.

COMPARATIVE EXAMPLE 1G

A developer was prepared in the same manner as in Example 1G, except that Aerosil 200 was not treated with γ-aminopropyltriethoxysilane and dimethyldichlorosilane, and development and transfer were also conducted similarly. As the result, only reversed images could be obtained, and the amount of triboelectric charges was −3.2 μc/g, exhibiting a negative charging characteristic.

COMPARATIVE EXAMPLE 2G

A developer was prepared in the same manner as in Example 1G except that no treatment with dimethyldichlorosilane was applied, and images were obtained similarly. At normal temperature and normal humidity, fog occurred little, but the image density was as low as 0.82 with conspicuous coarsening at the solid black portions. When successive copying test was conducted, the density was lowered to 0.61 on copying of 5000 sheets.

When images were obtained under the conditions of 35° C. and 85%, the image density was lowered to 0.63 with increase of fog, scattering of the toner and coarsening of the image, proving to be practically unuseful. The transfer efficiency was also as low as 70%. The weight of the toner layer per unit area was $0.70 \times 10^{-3}$ g/cm$^2$.

When the images were obtained under the conditions of 10° C. and 10% R.H., the image density was as low as 0.68, with excessive scattering, fog and coarsening, and transfer drop-off was markedly observed. Continuous image formation was effected until about 500 sheets was obtained when the density became 0.40 to make copying no longer practically possible. The toner weight per unit area at the initial stage was $1.7 \times 10^{-3}$ g/cm$^2$, which increased to $3.5 \times 10^{-3}$ g/cm$^2$ on copying of 500 sheets, with formation of wave pattern.

COMPARATIVE EXAMPLE 3G

Example 1G was repeated except that the amount of dimethyldichlorosilane was changed to 0.1% based on the silica. The hydrophobicity of the treated silica was found to be 15. Up to 100,000 sheets of copying under normal temperature and normal humidity in successive copying test, good images could be obtained without change of the toner weight of the toner layer per unit area. However, at 35° C. and 85%, the image density at the initial stage was 1.2, which was lowered to 0.78 on copying of 5,000 sheets. The toner layer, which was $1.4 \times 10^{-3}$ g/cm$^2$, was lowered to $0.75 \times 10^{-3}$ g/cm$^2$, on copying of 5,000 sheets.

After storage under the conditions of 10° C. and 10% for one month, successive copying test was conducted under the same conditions, whereby the image density at the initial stage was as good as 1.4, but ripple pattern occurred on copying of 5,000 sheets, with lowering of the image density to 0.62, and white streaks appeared on the image on copying of 7,000 sheets. At this stage, the weight of the toner layer was found to be increased to $4.0 \times 10^{-3}$ g/cm$^2$. The changes in weight of the toner layer per unit area during this operation are shown by FIG. 6(b).

EXAMPLES 2G-9G

When Example 1G was repeated except that the heat treatment temperatures of Aerosil 200 were changed to 430° C., 480° C., 500° C., 600° C., 700° C., 900° C., 1000° C., 1200° C., respectively, good results could be obtained. The hydrophobicity were found to be 50, 50, 55, 58, 70, 65, 68 and 68, respectively. The storage tests of respective samples for one month at 30° C. and 90% R.H. also yielded good results.

EXAMPLE 1H

| | |
|---|---|
| 3-Chloropropyl trimethoxysilane | 50 g |
| Methyl iodide | 0.5 g |
| 2-(Dimethylamino)ethyl methacrylate | 50 g |
| Dimethylformamide | 100 g |
| Sulfur | 0.5 g |

The above mixture was allowed to react under reflux at 95° C. for 50 hours to obtain a product:

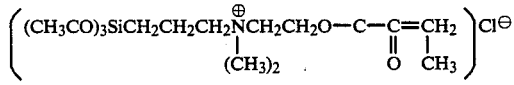

Next, 100 g of fine silica particles Aerosil 200 (produced by Nippon Aerosil Co.) were immersed in an aqueous solution containing 4 g of the above product, and the mixture was stirred at 60° C. for one hour. Then, the mixture was filtered and dried at 100° C. for 10 hours to obtain fine silica particles treated with a cation type unsaturated amine. The silica was placed into a Henschel mixer, and dimethyldichlorosilane was sprayed onto the silica under stirring to a quantity of 10%. High speed stirring was continued at room temperature for 2 hours, and the mixture was further stirred at 80° C. for 24 hours, followed by opening of the mixer to atmospheric pressure.

The above treated fine silica particles were added to the colored fine powder of Example 1F in an amount of 0.6%, followed by mixing in a Henschel mixer, to provide a developer.

Then, an OPC photosensitive member was applied with −6 KV corona discharging to be charged over the entire surface thereof, and irradiated with an original image to form electrostatic latent images thereon.

Development and transfer were conducted in the same manner as in Example 1F, except that this photosensitive member was combined with the developer carrying member of Example 1F and the developer as prepared above was employed. The image densities of the transferred images and the toner weights on the sleeve under various atmospheric conditions are shown below, and the developing characteristics including the results of successive copying test were satisfactory, being substantially equal to those of Example 1F.

| | Density | Toner weight |
|---|---|---|
| 22° C., 60% R.H. | 1.29 | $1.4 \times 10^{-3}$ g/cm$^2$ |
| 35° C., 85% R.H. | 1.25 | $1.35 \times 10^{-3}$ g/cm$^2$ |
| 10° C., 10% R.H. | 1.31 | — |

The changes in weight of the toner layer per unit area in successive copying test at lower temperature and lower humidity of 10° C. and 10% R.H. are shown in FIG. 7(a), which indicates that there was no substantial change.

COMPARATIVE EXAMPLE 1H

A developer was prepared in the same manner as in Example 1H, except that Aerosil 200 was not treated with the compound prepared in Example 1H or dimethyldichlorosilane, and development and transfer were also conducted similarly. As the result, only reversed images could be obtained.

COMPARATIVE EXAMPLE 2H

A developer was prepared in the same manner as in Example 1H except that no treatment with dimethyldichlorosilane was applied, and images were obtained similarly. At normal temperature and normal humidity, fog occurred little, but the image density was as low as 0.70, showing a tendency of coarsening. When successive copying test was conducted, the density was lowered to 0.53 on copying of 500 sheets. The initial weight of the toner layer per unit area was $1.3 \times 10^{-3}$ g/cm$^2$, which increased to $4.8 \times 10^{-3}$ g/cm$^2$ on copying of 500 sheets.

When the images were obtained under the conditions of 10° C. and 10% R.H., the image density was as low as 0.58, with excessive scattering, fog and coarsening, and transfer drop-off was markedly observed. Continuous image formation was effected until about 500 copies were obtained, when, spot-like irregularity was formed. The toner weight per unit area was $4.5 \times 10^{-3}$ g/cm$^2$.

COMPARATIVE EXAMPLE 3H

Example 1H was repeated except that the amount of dimethyldichlorosilane was changed to 0.3% based on the silica. The hydrophobicity of the treated silica was found to be 18. Up to 50,000 sheets of copying under normal temperature and normal humidity in successive copying test, good images could be obtained without change of the toner weight of the toner layer per unit area. However, at 35° C. and 85%, the image density at the initial stage was 1.0, which was lowered to 0.63 on copying of 5,000 sheets. The toner layer, which was $1.4 \times 10^{-3}$ g/cm$^2$ at the initial stage, was lowered to $0.63 \times 10^{-3}$ g/cm$^2$, on copying of 5,000 sheets. After storage under the conditions of 10° C. and 10% for one month, successive copying test was conducted under the same conditions, whereby the image density at the initial stage was as good as 1.3, but ripple pattern occurred on copying of 5,000 sheets, with lowering of the image density to 0.50, and white streaks appeared on the image on copying of 10,000 sheets. And, the weight of the toner layer was found to be increased to $4.3\times10^{-3}$ g/cm$^2$. The changes in weight of the toner layer per unit area during this operation are shown in FIG. 7(b).

EXAMPLES 2H–4H

When Example 1H was repeated under substantially the same conditions except that the amounts of the compound prepared in Example 1H and dimethyldichlorosilane treated on Aerosil 200 were changed to 0.3%, 1.0%; 1.0%, 1.0%; and 5.0%, 1.0%, respectively, good results could be obtained.

EXAMPLE 5H

| | |
|---|---|
| CH$_2$=C(CH$_3$)COOCH$_2$CH$_2$N(CH$_3$)$_2$ | 4 g |
| 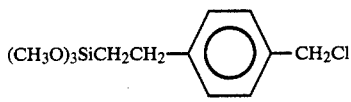 | 5 g |
| Methyl iodide | 0.5 g |
| t-Butyl alcohol | 50 g |
| Sulfur | 0.3 g |

The above mixture was refluxed at 100° C. for one hour to obtain a product:

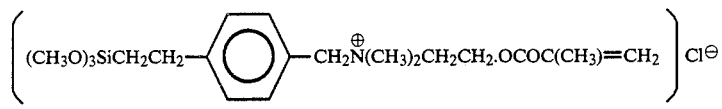

Subsequently, fine silica particles of Aerosil 200 were mixed in a Henschel mixer with the above product by spraying an aqueous solution thereof to a quantity of 5%. Then, the mixture was dried at 100° C. for 10 hours to obtain fine silica particles treated with a cation type unsaturated amine. The thus treated silica was again charged into a Henschel mixer, and dimethyldichlorosilane was sprayed onto the silica under stirring to a quantity of 5%. Then, the same treatments as in Example 1H were applied. The hydrophobicity was found to be 50.

| | |
|---|---|
| Polyethylene oxide | 100 parts |
| Carbon black | 3 parts |
| Magnetite | 70 parts |
| Nigrosine | 3 parts |

With the use of the above materials, the same procedure as described in Example 1H was repeated to obtain fine powder of 5 to 25μ. A developer was prepared by adding 0.3% of the above treated silica to the fine powder.

Next, images were obtained similarly as in Example 1H, followed by pressure fixing. The image density was found to be sufficiently high up to 1.41, and also faithful to the latent image. As the result of successive copying tests, the images obtained were practically satisfactory until copying of 100,000 sheets, and excellent characteristics were exhibited under the highet temperature and higher humidity conditions of 35° C. and 85% R.H., as well as under lower temperature and lower humidity conditions of 10° C. and 10% R.H.

EXAMPLE 1I

| | |
|---|---|
| Styrene-butyl methacrylate copolymer | 100 parts |
| Magnetite | 60 parts |
| Nigrosine | 3 parts |

The above materials were well blended in a blender and then kneaded on a twin roll heated to 150° C.. The kneaded product was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise γ-aminopropyl triethoxysilane diluted with alcohol to a treated quantity of 10.0% of the silane coupling agent based on the silica. The fine particles obtained were dried at 120° C. and thereafter placed again into a Henschel mixer, and dimethyl silicone oil (viscosity: 100 centipoise at 25° C.) was added to the silica under stirring to a quantity of 10.0%. The mixture was subjected to a high speed stirring at room temperature for 2 hours, followed further by stirring continued at 160° C. for 15 hours, and then the mixer was opened to atmospheric pressure. This mixture was further dried at room temperature under atmospheric pressure for 3 hours.

The thus treated fine silica particles were added to the above colored powder of 5 to 20μ, in an amount of 0.4%, followed by mixing by a Henschel mixer, to provide a developer.

Then, an OPC photosensitive member was applied with −6 KV corona discharging to be charged over the entire surface thereof, and irradiated with an original image to form electrostatic latent images thereon.

Development and transfer were conducted in the same manner as in Example 1F, except that this photosensitive member was combined with the developer carrying member of Example 1F and the developer as prepared above was employed. The image densities of the transferred images and the toner weights on the sleeve under various atmospheric conditions are shown below, and the developing characteristics including the results of successive copying test were satisfactory, being substantially equal to those of Example 1F.

| | Density | Toner weight |
|---|---|---|
| 22° C., 60% R.H. | 1.35 | $1.38\times10^{-3}$ g/cm$^2$ |
| 35° C., 85% R.H. | 1.30 | $1.3\times10^{-3}$ g/cm$^2$ |
| 10° C., 10% R.H. | 1.40 | — |

The changes in weight of the toner layer per unit area in successive copying test at lower temperature and lower humidity of 10° C. and 10% R.H. are shown in FIG. 8(a), which indicates that there was no substantial change.

COMPARATIVE EXAMPLE 1I

A developer was prepared in the same manner as in Example 1I, except that Aerosil 200 was not treated with γ-aminopropyltriethoxysilane and dimethyl silicone oil of 100 centipoise, and development and transfer were also conducted similarly. As the result, only reversed images could be obtained.

COMPARATIVE EXAMPLE 2I

A developer was prepared in the same manner as in Example 1I except that no treatment with dimethyl silicone oil was applied, and images were obtained similarly. At normal temperature and normal humidity, fog occurred little, but the image density was as low as 0.82, the line image was scattered with conspicuous coarsening at the solid black portion. When successive copying test was conducted, the density was lowered to 0.61 on copying of 5000 sheets. When the images were obtained unter the conditions of 35° C. and 85% R.H., the image density was lowered to 0.63 with increase of fog, scattering and coarsening, thus being unacceptable at all. The transfer efficiency was also as low as 70%. When the images were obtained under the conditions of 10° C. and 10% R.H., the image density became as low as 0.68 with excessive scattering, fog and coarsening, and transfer drop-off was markedly observed. The initial weight of the toner layer per unit area was $1.7 \times 10^{-3}$ g/cm², which increased to $3.5 \times 10^{-3}$ g/cm² on copying of 500 sheets, with ripple pattern formed.

COMPARATIVE EXAMPLE 3I

Example 1I was repeated except that the amount of dimethyl silicone oil was changed to 0.5% based on the silica. Until 100,000 sheets of copying under normal temperature and normal humidity in successive copying test, good images could be obtained without change of the toner weight of the toner layer per unit area. However, at 35° C. and 85%, the image density at the initial stage was 1.1, which was lowered to 0.80 on copying of 7,000 sheets. The toner layer, which was $1.4 \times 10^{-3}$ g/cm², was lowered to $0.75 \times 10^{-3}$ g/cm², on copying of 7,000 sheets.

After storage under the conditions of 10° C. and 10% for one month, successive copying test was conducted under the same conditions, whereby the image density at the initial stage was as good as 1.4, but ripple pattern occurred on copying of 5,000 sheets, with lowering of the image density to 0.75, and spot irregularities and white streaks appeared on the image on copying of 10,000 sheets. And, the weight of the toner layer was found to be increased to $4.0 \times 10^{-3}$ g/cm². The changes of the toner layer per unit area during this operation are shown in FIG. 8(b).

EXAMPLE 2I

When Example 1I was repeated under substantially the same conditions except that the silicone oil was changed to methyl hydrogen silicone oil (trade name: TSF 484, produced by Toshiba Silicone Co.), good results were obtained.

EXAMPLE 3I

When Example 1I was repeated under substantially the same conditions except for replacing γ-aminopropyltriethoxysilane with N,N-dimethylaminophenyl triethoxysilane, good results were obtained.

EXAMPLE 1J

| | |
|---|---|
| Styrene-butadiene copolymer (70:30) | 100 parts |
| Magnetite | 60 parts |
| Nigrosine | 4 parts |

The above materials were well blended in a blender and then kneaded on a twin roll heated to 150° C. The kneaded produce was left to cool, coarsely crushed by a cutter mill, pulverized by means of a micropulverizer with a jet air stream and further subjected to classification by use of a wind force classifier to obtain colored fine powder of 5 to 20μ.

As the next step, fine silica particles Aerosil 200 (produced by Nippon Aerosil Co.) were placed in a sealed type Henschel mixer heated to 70° C. and stirred at a high speed, while adding to the silica dropwise isopropyl tri-isostearoyl titanate diluted with alcohol to a treated quantity of 2.0% of the titanium coupling agent based on silica. The fine particles obatined were dried at 120° C.

A developer was prepared by adding the treated fine silica particles to the above fine colored powder in an amount of 0.6%, followed by mixing by a Henschel mixer.

Then, an OPC photosensitive member was applied with −6 KV corona discharging to be charged over the entire surface thereof, and irradiated with an original image to form electrostatic latent images thereon.

Development and transfer were conducted in the same manner as in Example 1F, except that this photosensitive member was combined with the developer carrying member of Example 1F and the developer as prepared above was employed. The image densities of the transferred images and the toner weights on the sleeve under various atmospheric conditions are shown below, and the developing characteristics including the results of successive copying test were satisfactory, being substantially equal to those of Example 1F.

| | Density | Toner weight |
|---|---|---|
| 22° C., 60% R.H. | 1.40 | $1.5 \times 10^{-3}$ g/cm² |
| 35° C., 85% R.H. | 1.30 | $1.43 \times 10^{-3}$ g/cm² |
| 10° C., 10% R.H. | 1.43 | — |

COMPARATIVE EXAMPLE 1J

A developer was prepared in the same manner as in Example 1J, except that Aerosil 200 was not treated with isopropyl tri-isostearoyl titanate, and development and transfer were also conducted similarly. As the result, only reversed images could be obtained.

EXAMPLES 2J-7J

Example 1J was repeated except that, in place of isopropyl tri-isostearoyl titanate, there were employed as titanate type coupling agents, respectively, isopropyl di-isostearoyltamylphenyl titanate (Example 2J), isopropyl tridodecylbenzenesulfonyl titanate (Example 3J), isopropyltri(dioctylphosphate)titanate (Example 4J), isopropyl-4-aminobenzenesulfonyldi(dodecylbenzenesulfonyl)titanate (Example 5J), isopropyltri(N-ethylamino-ethylamino)titanate (Example 6J) and isostearoyl methacryloxyacetate titanate (Example 7J). Good results were obtained in each case.

What is claimed is:

1. A developer comprising a binder resin, a colorant and a positive charge controller, said positive charge controller comprising fumed silica particles treated with a coupling agent having a hydrolyzable group and a non-hydrolyzable organic group bonded to a tetravalent center atom of Si or Ti, said positive charge controller having a hydrophobicity within the range of from 30 to 80 as measured by the methanol titration test, in which said coupling agent is a silane or titanate coupling agent selected from the group consistng of formula compounds (1), (2) or (3), wherein formula (1) compounds have the formula:

 (1)

wherein R is an alkoxy group or a chlorine atom; m and n are integers satisfying the relation of m+n=4; Y is an organic group containing at least one of amino, vinyl, glycidoxy, mercapto, methacryl, and ureido groups;

wherein formula 2 compounds are cation type unsaturated amino-functional silanes selected from the compounds represented by formula 2 as follows:

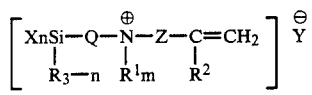 (2)

wherein X is a hydroxyl group or a hydrolyzable group; R is an alkyl having 1 to 6 carbon atoms; n is an integer of 1 to 3; Q is a divalent hydrocarbon group or an organic group containing oxygen in the form of

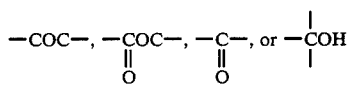

or nitrogen in the form of $R^2N=$group; $R^1$ is a hydrogen atom, an alkyl group having 1 to 6 carbon atoms or a heterocyclic organic group having a nitrogen in the ring; m is 2; Z is a divalent organic group having a conjugated double bond with

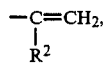

and bonded through C—N bonding to the nitrogen atom; $R^2$ is hydrogen atom or an alkyl having 1 to 6 carbon atoms; and Y is an acid anion or a hydrolyzed product of said cation type unsaturated amino-functional silane; and wherein formula 3 compounds are titanium compounds represented by the formula (3) as follows:

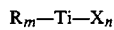 (3)

wherein m and n are 1 and 2, respectively, or 4 and 2, respectively; R is an alkoxy group,

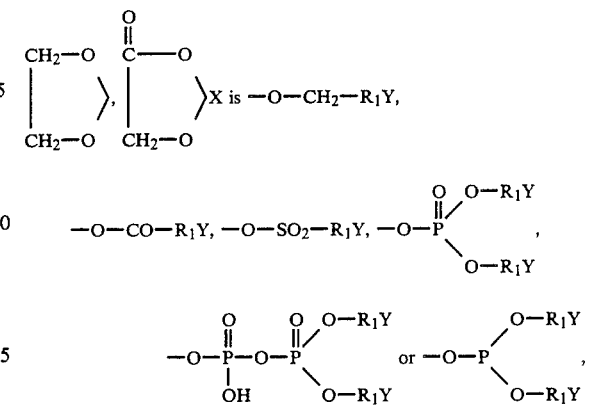

wherein in the above formulae, $R_1$ is a saturated or unsaturated divalent aliphatic group having 1 to 31 carbon atoms or a divalent aromatic hydrocarbylene group; Y is a hydrogen atom or an amino group; and a plurality of X, $R_1$ and Y existing in the same compound being the same or different, respectively.

2. A developer according to claim 1, wherein the positive charge controller has a hydrophobicity degree of 30 to 80 by treating the fumed silica particles with the coupling agent having Si as the center atom and thereafter treating said particles with a hydrophobicity modifying agent selected from organic silicon compounds and silicone oils.

3. A developer according to claim 1 wherein the positive charge controller is obtained by subjecting the fumed silica particles to a heat treatment prior to the treatment with the coupling agent.

4. A developer according to claim 1, wherein the developer further contains magnetic material powder.

5. A developer according to claim 1, wherein the developer comprises binder particles having a colorant dispersed therein and the particles of the positive charge controller adhering on said binder particle surfaces.

6. A developing process, which comprises providing an electrostatic image bearing member for bearing electrostatic images on its surface and a developer carrying member arranged with a predetermined gap therebetween, permitting an insulating magnetic positively charged developer of claim 4 to be carried on said developer carrying member in a thickness thinner than said gap, and transferring said developer to said electrostatic image-bearing member thereby effect development.

7. A developer comprising a binder resin, a colorant and a positive charge controller, said positive charge controller comprising fumed silica particles treated with a coupling agent having a hydrolyzable group and a non-hydrolyzable organic group bonded to a tetravalent center atom of Si or Ti, said positive charge controller having a hydrophobicity within the range of from 30 to 80 as measured by the methanol titration test, in which said coupling agent is a silane or titanate coupling agent selected from the group consisting of formula compounds (1), (2) or (3), wherein formula (1) compounds have the formula:

 (1)

wherein R is an alkoxy group or a chlorine atom; m and n are integers satisfying the relation of m+n=4; Y is an organic group containing at least one of amino, vinyl, glycidoxy, mercapto, methacryl, and ureido groups;

wherein formula 2 compounds are cation type unsaturated amino-functional silanes selected from the compounds represented by formula (2) as follows:

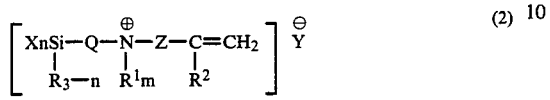 (2)

wherein X is a hydroxyl group or a hydrolyzable group; R is an alkyl having 1 to 6 carbon atoms; n is an integer of 1 to 3; Q is a divalent hydrocarbon group or an organic group containing oxygen in the form of

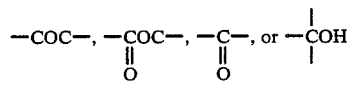

or nitrogen in the form of $R^2N=$group; $R^1$ is a hydrogen atom, an alkyl group having 1 to 6 carbon atoms or a heterocyclic organic group having a nitrogen atom in the ring; m is 2; Z is a divalent organic group having a conjugated double bond with

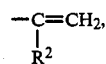

bonded through C—N bonding to the nitrogen atom; $R^2$ is a hydrogen atom or an alkyl having 1 to 6 carbon atoms; and Y is an acid anion or a hydrolyzed product of said cation type unsaturated amino-functional silane; and wherein formula 3 compounds are titanium combounds represented by the formula (3) as follows:

$R_m$—Ti—$X_n$ (3)

wherein m and n are 1 and 2, 1 and 3, or 4 and 2, respectively; R is an alkoxy group,

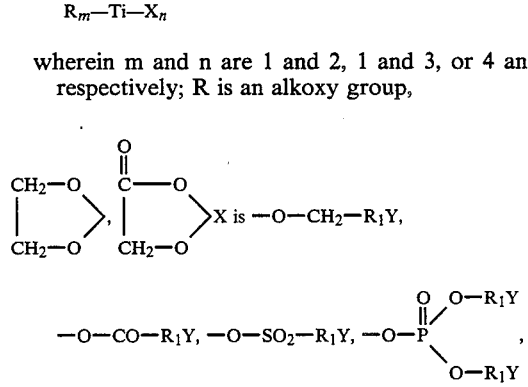

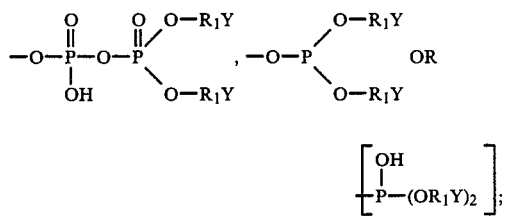

wherein the above formulae, $R_1$ is a saturated or unsaturated divalent aliphatic group having 1 to 31 carbon atoms or a divalent aromatic hydrocarbylene group; Y is a hydrogen atom or an amino group; and a plurality of X, $R_1$ and Y existing in the same compound being the same or different, respectively.

8. A developer according to claim 7, wherein the positive charge controller has a hydrophobicity degree of 30 to 80 by treating the fumed silica particles with the coupling agent having Si as the center atom and thereafter treating said particles with a hydrophobicity modifying agent selected from organic silicon compounds and silicone oils.

9. A developer according to claim 7, wherein the positive charge controller is obtained by subjecting the fumed silica particles to a heat treatment prior to the treatment with the coupling agent.

10. A developer according to claim 7, wherein the developer further contains magnetic material powder.

11. A developer according to claim 7, wherein the developer comprises binder particles having a colorant dispersed therein and the particles of the positive charge controller adhering on said binder particle surfaces.

12. A developer according to claim 7, wherein said coupling agent is a silane coupling agent selected from the formula (1) compounds.

13. A developer according to claim 7, wherein said coupling agent is a silane coupling agent selected from the formula (2) compounds.

14. A developer according to claim 7, wherein said coupling agent is a titanate coupling agent selected from the formula (3) compounds.

15. A developer according to claim 7, wherein the group

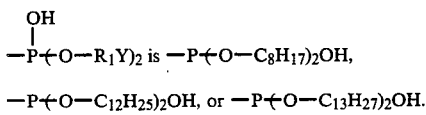

16. A developer according to claim 15, wherein said coupling agent is selected from the group consisting of

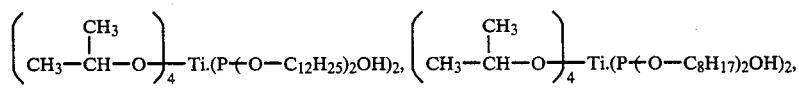

-continued

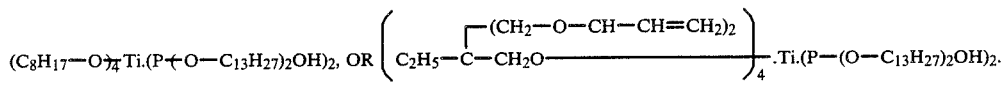

17. A developing process, which comprises providing an electrostatic image bearing member for bearing electrostatic images on its surface and a developer carrying member arranged with a predtermined gap therebetween, permitting an insulating magnetic positively-charged developer of claim 10 to be carried on said developer carrying member in a thickness thinner than said gap, and transferring said developer to said electrostatic image-bearing member thereby to effect development.

18. A developer comprising a binder resin, a colorant and a positive charge controller, said positive charge controller comprising formed silica particles treated with a titanate coupling agent selected from the group consisting of:

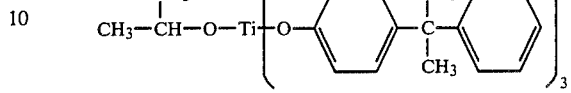

and

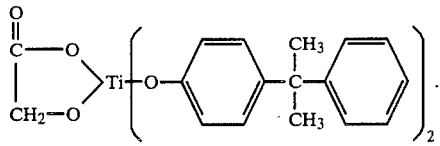

* * * * *